US007942923B2

(12) United States Patent
Gregorich

(10) Patent No.: US 7,942,923 B2
(45) Date of Patent: May 17, 2011

(54) OVERLAPPED STENTS FOR SCAFFOLDING, FLEXIBILITY AND MRI COMPATIBILITY

(75) Inventor: Daniel Gregorich, Mound, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1272 days.

(21) Appl. No.: 11/120,916

(22) Filed: May 3, 2005

(65) Prior Publication Data
US 2005/0278019 A1 Dec. 15, 2005

Related U.S. Application Data

(63) Continuation of application No. 10/864,665, filed on Jun. 9, 2004.

(51) Int. Cl.
*A61F 2/86* (2006.01)
(52) U.S. Cl. ........................................ 623/1.16; 623/1.22
(58) Field of Classification Search .................. 623/1.16, 623/1.15, 1.22, 1.44, 1.18
See application file for complete search history.

(56) References Cited

U.S. PATENT DOCUMENTS

| 4,800,882 | A | | 1/1989 | Gianturco | 128/343 |
|---|---|---|---|---|---|
| 5,064,435 | A | | 11/1991 | Porter | 623/12 |
| 5,091,205 | A | | 2/1992 | Fan | 427/2 |
| 5,170,789 | A | | 12/1992 | Narayan et al. | 128/653.5 |
| 5,405,377 | A | | 4/1995 | Cragg | 623/1 |
| 5,445,151 | A | | 8/1995 | Darrow et al. | 128/653.3 |
| 5,466,242 | A | * | 11/1995 | Mori | 606/198 |
| 5,617,878 | A | | 4/1997 | Taheri | 128/898 |
| 5,744,958 | A | | 4/1998 | Werne | 324/318 |
| 5,749,825 | A | | 5/1998 | Fischell et al. | 600/3 |
| 5,755,781 | A | | 5/1998 | Jayaraman | 623/1 |
| 5,817,017 | A | | 10/1998 | Young et al. | 600/433 |
| 5,824,045 | A | | 10/1998 | Alt | 623/1 |
| 5,843,120 | A | | 12/1998 | Israel et al. | 606/198 |
| 5,865,723 | A | | 2/1999 | Love et al. | 600/36 |

(Continued)

FOREIGN PATENT DOCUMENTS

CA 2 425 813 4/2002

(Continued)

OTHER PUBLICATIONS

U.S. Appl. No. 10/864,665, filed Jun. 9, 2004, Gregorich.

Primary Examiner — Anhtuan T Nguyen
Assistant Examiner — Ryan J Severson
(74) Attorney, Agent, or Firm — Vidas, Arrett & Steinkraus P.A.

(57) ABSTRACT

A tubular insert for a vessel comprises an inner stent and an outer stent. At least a portion of the inner stent is disposed within the outer stent. The outer stent has a longitudinal axis and is constructed to be free of any closed loops which are electrically conductive and which are disposed about the longitudinal axis such that the longitudinal axis passes through the closed loop. The inner stent has a longitudinal axis and is constructed so as to be free of any closed loops which are electrically conductive and which are disposed about the longitudinal axis such that the longitudinal axis passes through the closed loop. There is a substantially electrically non-conductive connection between the inner and outer stents. Desirably, a wall surface is defined by the outer and inner stents, and there are no closed, electrically conductive loops in the wall surface of the tubular insert.

2 Claims, 27 Drawing Sheets

U.S. PATENT DOCUMENTS

| | | | |
|---|---|---|---|
| 5,916,264 A | 6/1999 | Von Oepen et al. | 623/1 |
| 6,042,597 A | 3/2000 | Kveen et al. | 606/198 |
| 6,099,559 A | 8/2000 | Nolting | 623/1.16 |
| 6,120,522 A | 9/2000 | Vrba et al. | 606/190 |
| 6,120,535 A | 9/2000 | McDonald et al. | 623/1.39 |
| 6,238,340 B1 | 5/2001 | Alt et al. | 600/431 |
| 6,245,100 B1 | 6/2001 | Davila et al. | 623/1.13 |
| 6,280,385 B1 | 8/2001 | Melzer et al. | 600/423 |
| 6,325,823 B1 * | 12/2001 | Horzewski et al. | 623/1.16 |
| 6,361,558 B1 * | 3/2002 | Hieshima et al. | 623/1.16 |
| 6,364,904 B1 * | 4/2002 | Smith | 623/1.22 |
| 6,409,754 B1 | 6/2002 | Smith et al. | 623/1.16 |
| 6,428,569 B1 | 8/2002 | Brown | 623/1.15 |
| 6,487,437 B1 | 11/2002 | Viswanathan et al. | 600/423 |
| 6,506,201 B2 | 1/2003 | Di Caprio et al. | 606/192 |
| 6,551,351 B2 | 4/2003 | Smith et al. | 623/1.16 |
| 6,585,755 B2 | 7/2003 | Jackson et al. | 623/1.15 |
| 6,695,877 B2 | 2/2004 | Brucker et al. | 623/1.16 |
| 2001/0044650 A1 | 11/2001 | Simso et al. | 623/1.16 |
| 2002/0013617 A1 | 1/2002 | Matsutani et al. | 623/1.15 |
| 2002/0173840 A1 | 11/2002 | Brucker et al. | 623/1.16 |
| 2002/0188345 A1 * | 12/2002 | Pacetti | 623/1.15 |
| 2003/0114919 A1 * | 6/2003 | McQuiston et al. | 623/1.15 |
| 2003/0212449 A1 | 11/2003 | Cox | 623/1.15 |
| 2004/0015229 A1 | 1/2004 | Fulkerson et al. | 623/1.22 |
| 2004/0039438 A1 | 2/2004 | Alt | 623/1.15 |
| 2004/0073291 A1 | 4/2004 | Brown et al. | 623/1.15 |
| 2004/0249440 A1 | 12/2004 | Bucker et al. | 623/1.15 |
| 2005/0033407 A1 | 2/2005 | Weber et al. | 623/1.15 |

FOREIGN PATENT DOCUMENTS

| | | |
|---|---|---|
| WO | 93/13825 | 7/1993 |
| WO | 96/26689 | 9/1996 |
| WO | 01/08600 | 2/2001 |
| WO | 03/015662 | 2/2003 |
| WO | WO 03/099168 | 12/2003 |
| WO | WO 2005/018500 | 3/2005 |
| WO | WO 2005/053575 | 6/2005 |
| WO | WO 2005/072653 | 8/2005 |

* cited by examiner

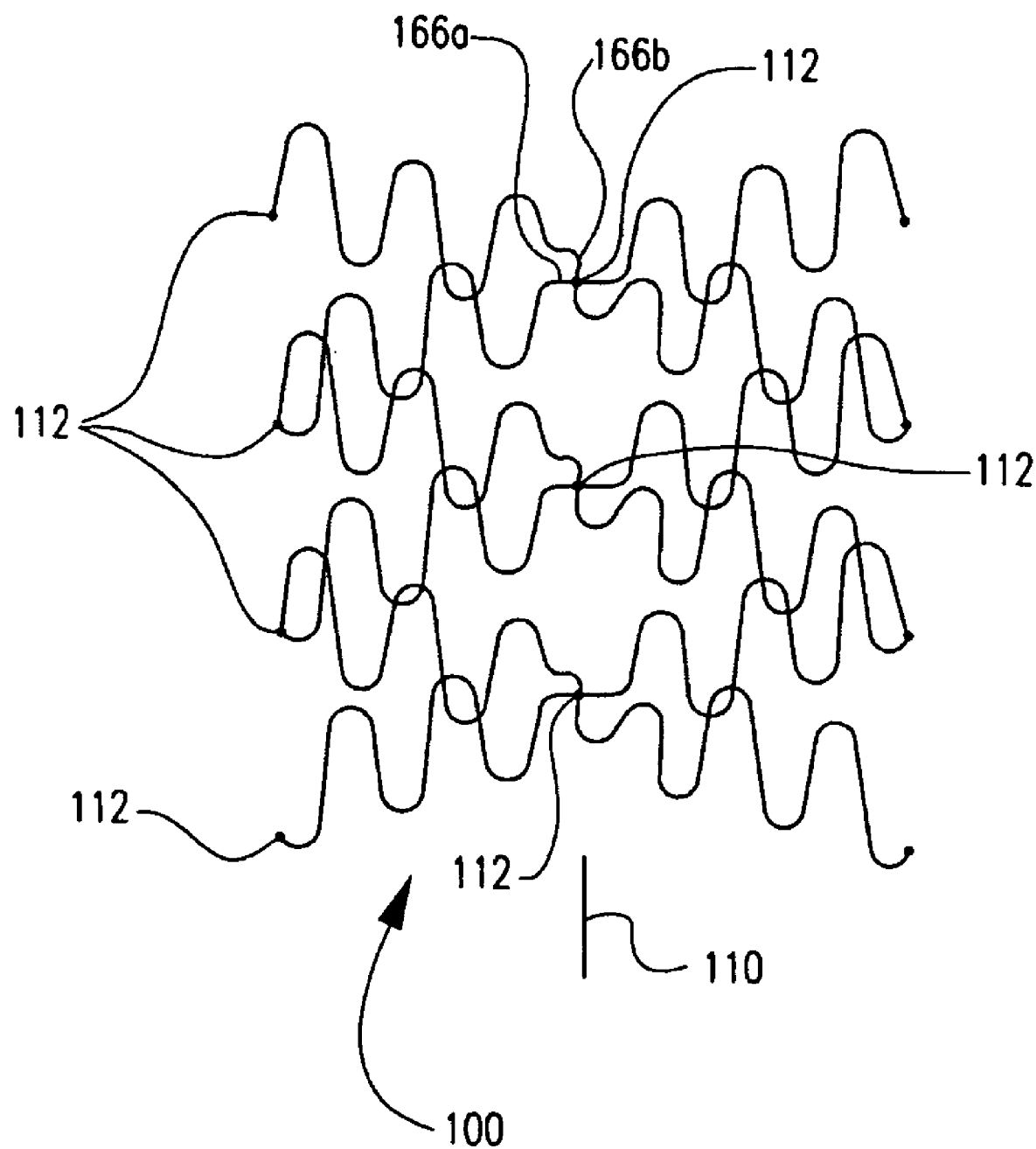

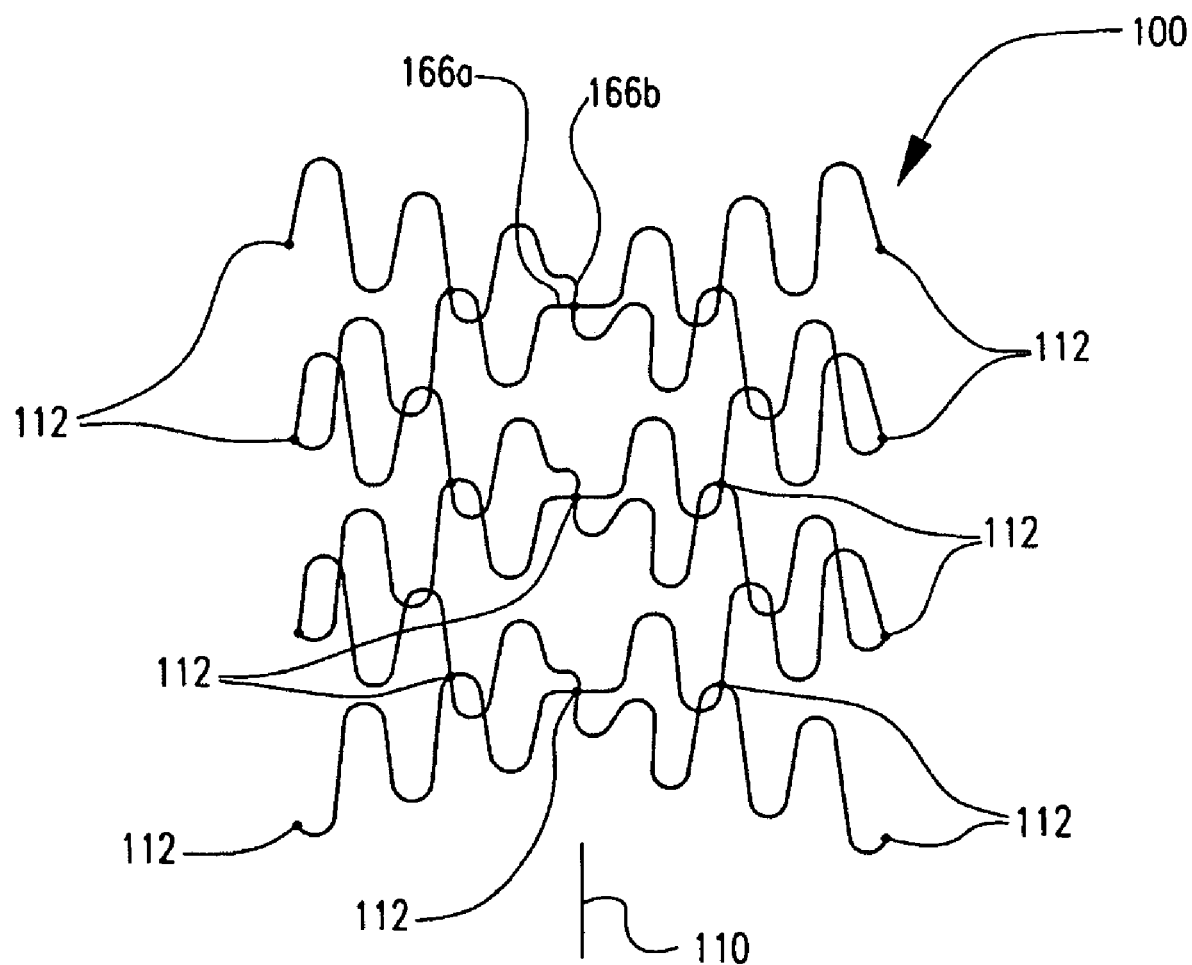

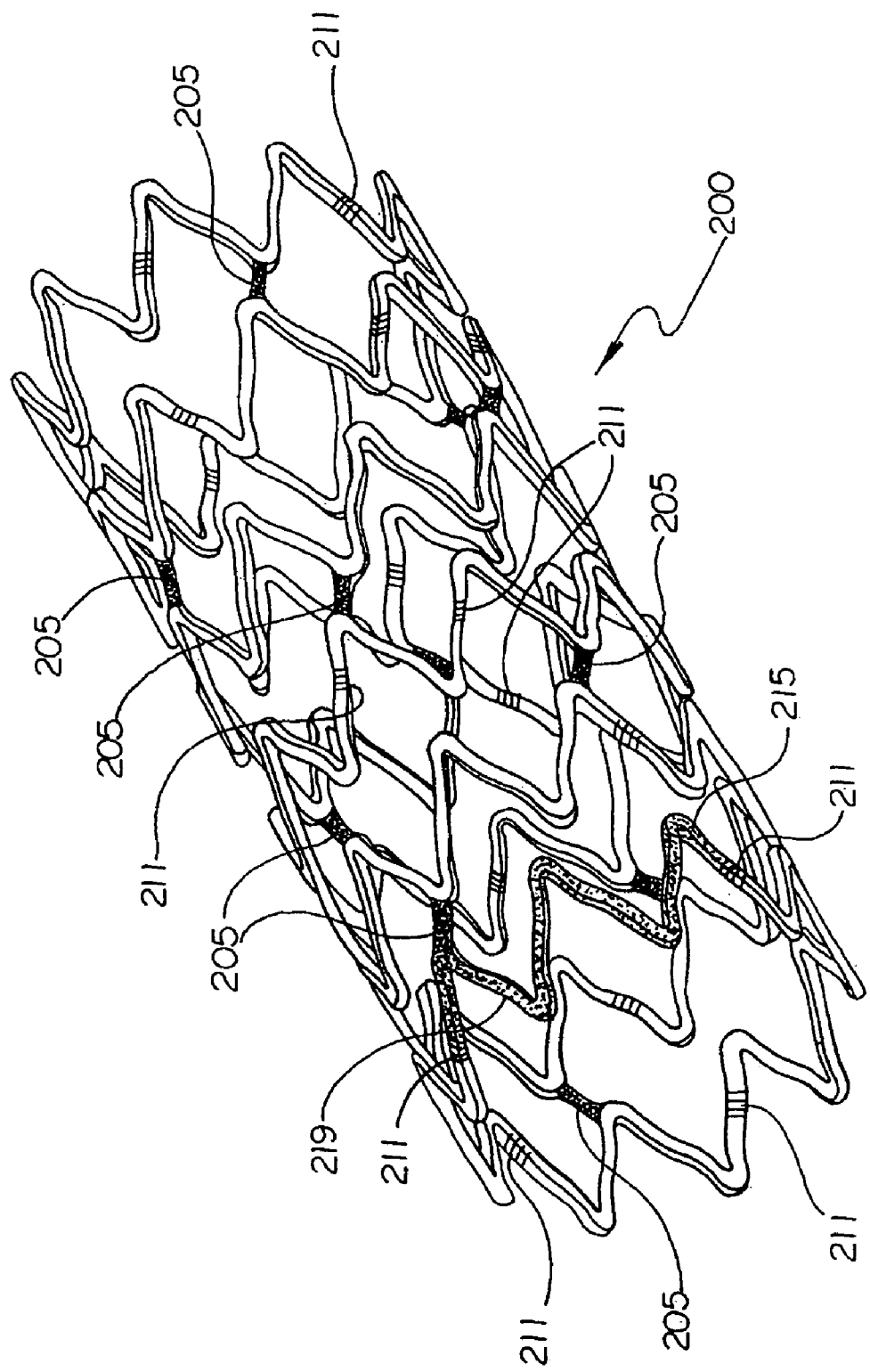

OVERLAPPED STENTS FOR SCAFFOLDING, FLEXIBILITY AND MRI COMPATIBILITY

CROSS-REFERENCE TO RELATED APPLICATIONS

This application is a Continuation application from Application No. 10/864,665, filed Jun. 9, 2004, the contents of which is hereby incorporated by reference

BACKGROUND OF THE INVENTION

A stent is a generally tubular device that is used to support a bodily lumen. A stent is typically delivered to a desired bodily location via a catheter.

Magnetic resonance imaging (MRI) has been widely used to image various parts of the body. One of the uses of MRI has been to image blood flow. It is, therefore, desirable for stents to be MRI compatible to allow for imaging of vessels in the region of a stent. Although there has been a great deal of activity focusing on the choice of materials for MRI compatible stents, other factors in the design of the stent must be considered as well.

For example, a stent that is made from an electrically conductive material that is formed in electrically conductive loops which extend fully around the longitudinal axis of the stent, as shown by way of example at 50 in FIG. 1, may facilitate the formation of eddy currents when the region of the body in which the stent is located is imaged. Similarly, the presence of closed, electrically conductive loops which extend in a longitudinal direction in the wall, as shown by way of example at 54 in FIG. 1, also may result in eddy currents. Eddy currents, however, are know to cause distortions in MRI images.

While many helical stents avoid the problem of electrically conductive loops which extend fully about the longitudinal axis, helical stents may have less compression resistance as compared with stents having circumferential bands which extend fully about the longitudinal axis. The scaffolding provided by helical stents is also less than that provided by many of the stents having closed circumferential bands.

Generally, there is a tradeoff between scaffolding and side branch access. A stent with a larger, more open geometry will have an improved side branch access and expandability but poorer scaffolding. Smaller, tight geometry results in better scaffolding, but poor side branch access and expandability.

There remains a need for MRI compatible stents with innovative designs which combine excellent scaffolding, compression resistance and side branch access while at the same time providing reduced MRI distortions.

All US patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 CFR 1.72.

BRIEF SUMMARY OF EMOBIDMENT(S) OF THE INVENTION

In one embodiment, the invention is directed to a tubular insert for a bodily vessel. The insert comprises an inner stent and an outer stent. At least a portion of the inner stent is disposed within the outer stent. The outer stent has a longitudinal axis and is constructed so as to be free of any closed loops which are electrically conductive and which are disposed about the longitudinal axis such that the longitudinal axis passes through the closed loop. The inner stent has a longitudinal axis and is constructed so as to be free of any closed loops which are electrically conductive and which are disposed about the longitudinal axis such that the longitudinal axis passes through the closed loop. There is a substantially electrically non-conductive connection between the inner stent and the outer stent. Desirably, where a wall surface is defined by the outer and inner stents, there are no closed, substantially electrically conductive loops in the wall surface of the tubular insert. Typically, at least portion of both the inner and outer stents will be made of metal.

The invention is also directed to a method of imaging a tubular medical device where the tubular medical device is in the form of an outer stent and an inner stent. At least a portion of the inner stent is disposed within the outer stent. The outer stent has a longitudinal axis and is constructed so as to be free of any closed loops which are electrically conductive and are disposed about the longitudinal axis such that the longitudinal axis passes through the closed loop. The inner stent has a longitudinal axis and is constructed so as to be free of any closed loops which are electrically conductive; and are disposed about the longitudinal axis such that the longitudinal axis passes through the closed loop. There is a substantially electrically non-conductive connection between the inner stent and the outer stent. Desirably, where a wall surface is defined by the outer and inner stents, there are no closed, substantially electrically conductive loops in the wall surface of the tubular insert. The method comprises the steps of disposing the tubular medical device within a magnetic resonance imager; using the magnetic resonance imager to obtain a magnetic resonance image of the tubular medical device and removing the tubular medical device from the magnetic resonance imager.

In one embodiment, the inventive method of imaging a tubular medical device is carried with the tubular medical device located within a living body when it is disposed within the magnetic resonance imager. In another embodiment, the tubular medical device is not located within a living body when it is disposed within the magnetic resonance imager.

The invention is also directed to a method of manufacturing a tubular medical device comprising the steps of providing a first stent and a second stent, disposing at least a portion of the second stent within the first stent and connecting the first stent and the second stent together via a connection which is substantially electrically non-conductive. The first stent has a longitudinal axis and is constructed so as to be free of any closed loops which are electrically conductive and disposed about the longitudinal axis such that the longitudinal axis passes through the closed loop. The second stent has a longitudinal axis and is constructed so as to be free of any closed loops which are electrically conductive and disposed about the longitudinal axis such that the longitudinal axis passes through the closed loop. There is a substantially electrically non-conductive connection between the first stent and the second stent. Desirably, where a wall surface is defined by the first and second stents, there are no closed, substantially electrically conductive loops in the wall surface of the tubular medical device.

In any of the inventive devices and methods described above and below, desirably there are a plurality of substantially electrically non-conductive connections between the inner stent and the outer stent or between the first stent and the second stent.

Typically, the inner stent or first stent will be a helical stent and the outer stent or second stent will be a helical stent. Where helical stents are used, one of the outer stent (or first stent) and inner stent (or second stent) extends generally clockwise about the longitudinal axis of the stent from one end of the stent to another and the other of the outer stent (or first stent) and inner stent (or second stent) extends in a generally counterclockwise direction about the longitudinal axis of the stent.

It is within the scope of the invention to use other types of stent as well for the outer (or first) and inner (or second) stents. For example, the outer or first stent may include a rib which runs along the length of the stent and a plurality of outer arms extending therefrom where the outer arms extend only part of the way about the circumference of the stent. The inner or second stent may include a rib which runs along the length of the stent and a plurality of inner arms extending therefrom where the inner arms extend only part of the way about the circumference of the stent.

As another example, the outer or first stent may include a plurality of interconnected loops which extend at an oblique or perpendicular angle relative to the longitudinal axis of the stent with the loops extending only part of the way about the longitudinal axis of the stent. The inner or second stent may include a plurality of interconnected loops which extend at an oblique or perpendicular angle relative to the longitudinal axis of the stent with the loops extending only part of the way about the longitudinal axis of the stent.

Desirably, the tubular medical device or insert will have a plurality of cells where each cell is defined by a portion of the outer or first stent, a portion of the inner or second stent and at least two connections between the outer or first stent and the inner or second stent.

The non-conductive connection(s) between stents will typically comprise one or more plastics, adhesives, composites, ceramic or combinations thereof.

Desirably, at least one and more desirably both the outer (or first) stent and the inner (or second) stent are made from a magnetic resonance compatible material. The inner or second and outer or first stents may both be made of a conductive material with a non-conductive material disposed thereabout.

These and other embodiments which characterize the invention are pointed out with particularity in the claims annexed hereto and forming a part hereof. However, for a better understanding of the invention, reference should be made to the drawings which form a further part hereof and the accompanying descriptive matter, in which there is illustrated and described embodiments of the invention.

BRIEF DESCRIPTION OF THE SEVERAL VIEWS OF THE DRAWINGS

A detailed description of the invention is hereafter described with specific reference being made to the drawings in which:

FIG. 5c shows an inventive tubular insert which has been cut open along a line parallel to the longitudinal axis of the stent and laid flat.

FIG. 5d shows another inventive tubular insert which has been cut open along a line parallel to the longitudinal axis of the stent and laid flat.

FIG. 9 shows another stent for use in the invention.

DETAILED DESCRIPTION OF THE INVENTION

Figure 1:
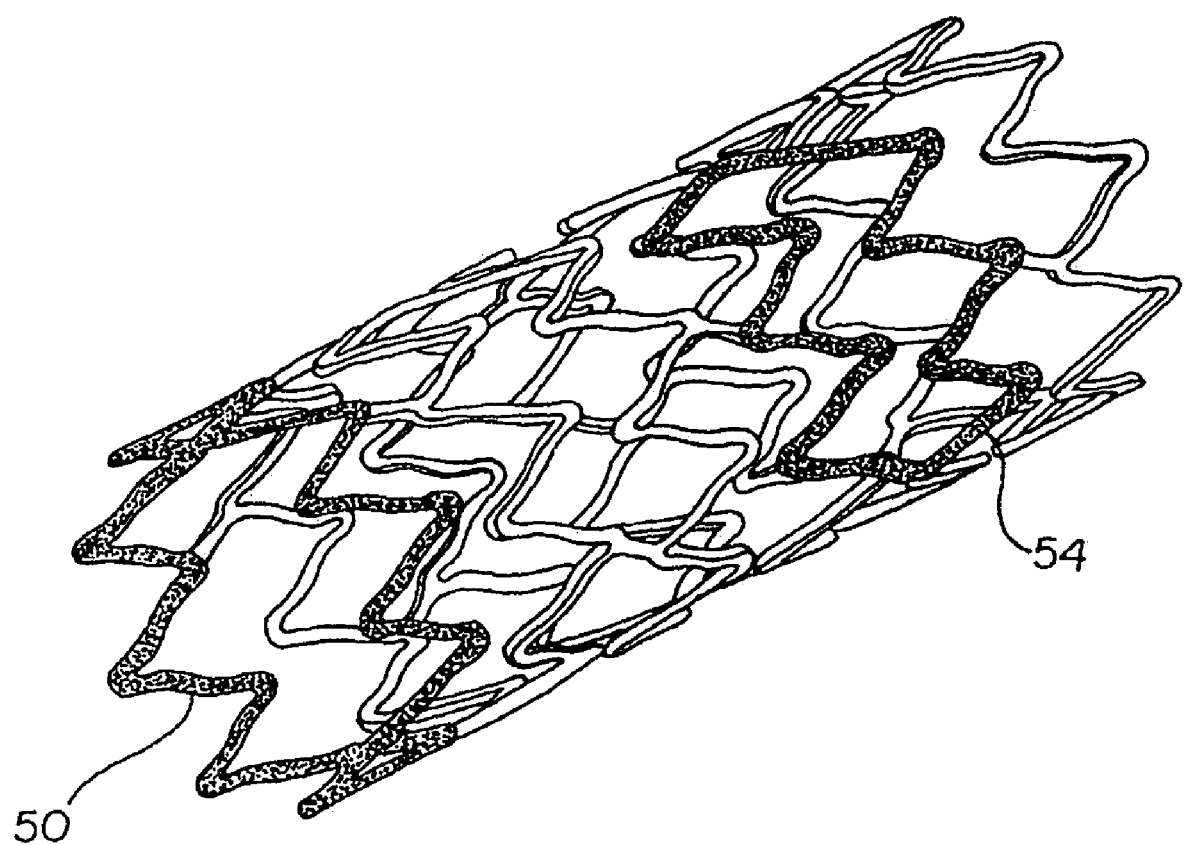
FIG. 1 shows a prior art stent.

While this invention may be embodied in many different forms, there are described in detail herein several specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In one embodiment, the invention is directed to a tubular insert for a bodily vessel. The insert, as shown generally in the flat at 100 in FIG. 2c, comprises an inner stent 104 and an outer stent 108. At least a portion of inner stent 104 is disposed within the outer stent 108. The outer stent has a longitudinal axis 110 and is constructed so as to be free of any closed loops which are electrically conductive and which are disposed about the longitudinal axis such that the longitudinal axis passes through the closed loop. The inner stent has a longitudinal axis 110 and is constructed so as to be free of any closed loops which are electrically conductive and which are disposed about the longitudinal axis such that the longitudinal axis passes through the closed loop. There is at least one and desirably, a plurality of substantially electrically non-conductive 112 connections between the inner stent and the outer stent. Desirably, where a wall surface is defined by the outer and inner stents, there are no closed, substantially electrically conductive loops in the wall surface of the tubular insert.

Figure 2A:
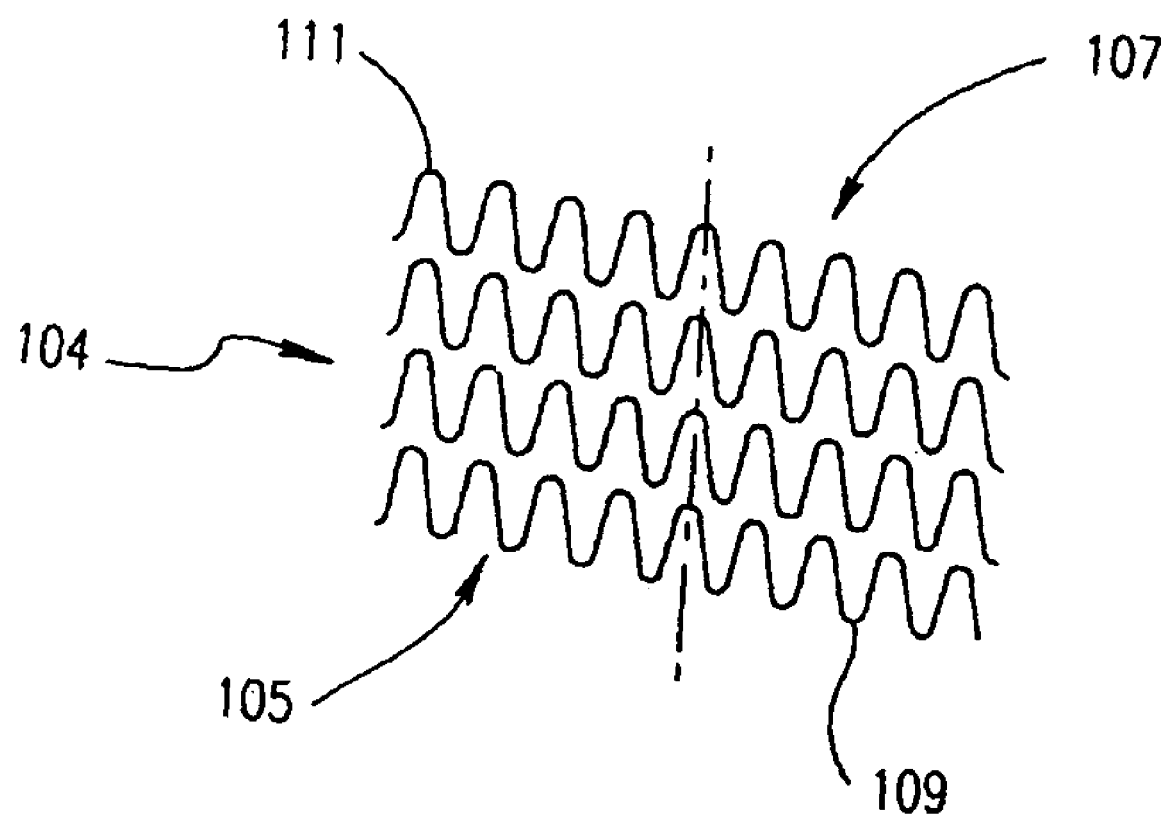
FIG. 2a shows a stent which has been cut open along a line parallel to the longitudinal axis of the stent and laid flat. The stent is for use as a component of the inventive tubular inserts.
Figure 2B:
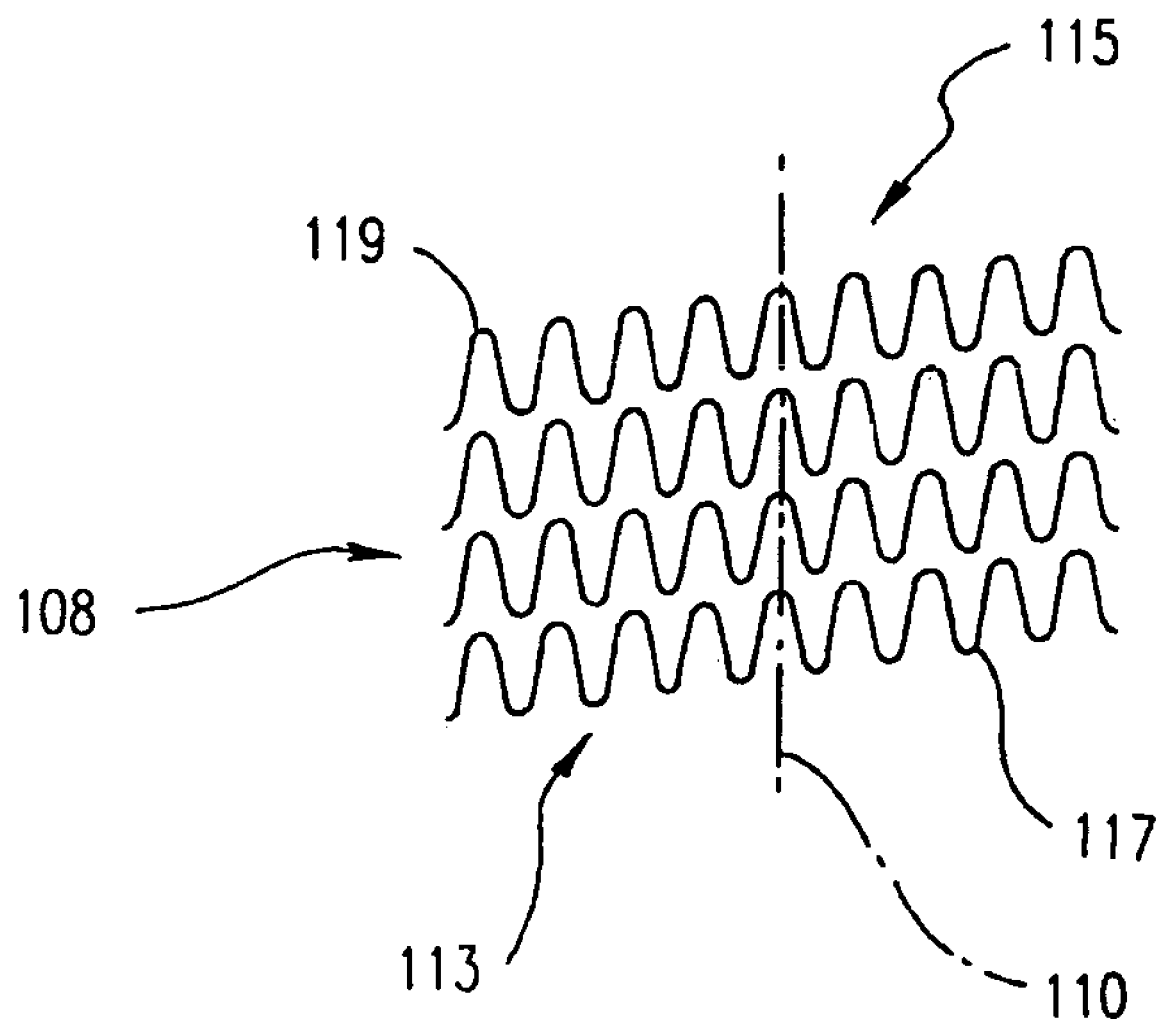
FIG. 2b shows a stent which has been cut open along a line parallel to the longitudinal axis of the stent and laid flat. The stent is for use as a component of the inventive tubular inserts.
Figure 2C:
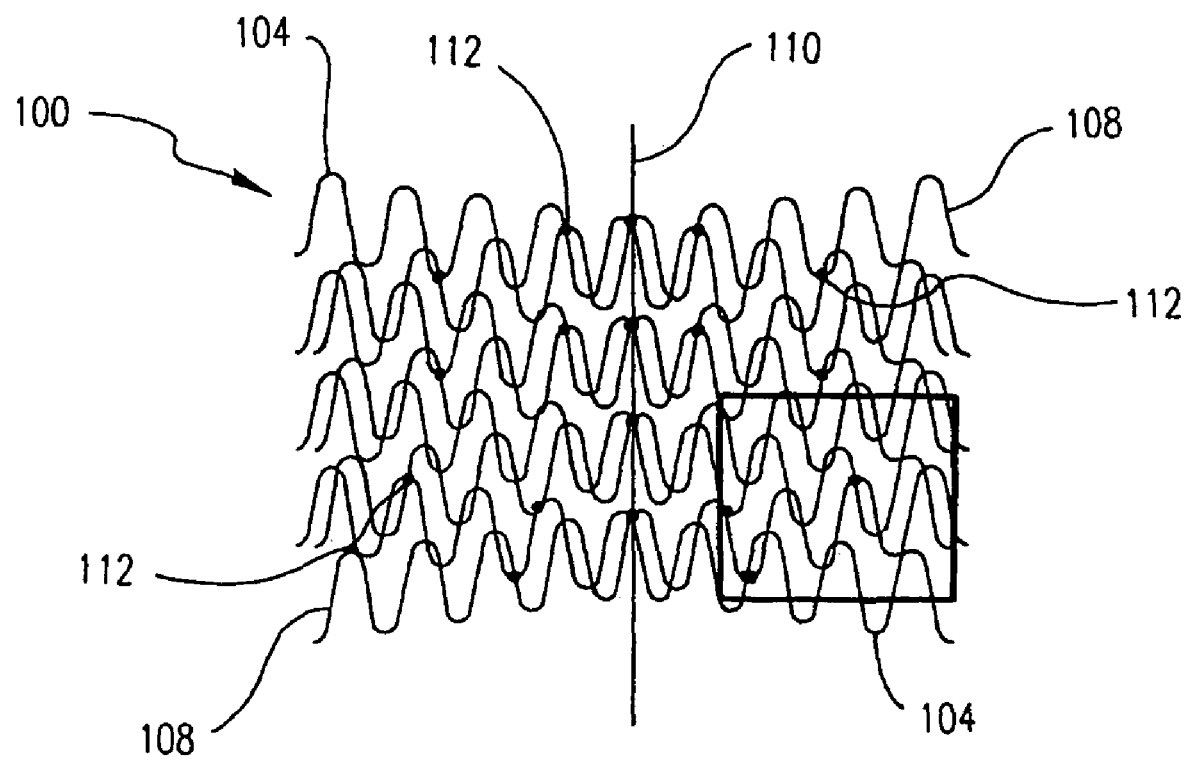
FIG. 2c shows an inventive tubular insert which has been cut open along a line parallel to the longitudinal axis of the stent and laid flat.

Typically, the inner stent or first stent will be a helical stent, as shown schematically in FIG. 2a and the outer stent or second stent will be a helical stent as shown schematically in FIG. 2b. Inner helical stent 104 has a proximal end 105 and a distal end 107 and a plurality of proximal turns 109 and distal turns 111. Outer helical stent 108 has a proximal end 113 and a distal end 115 and a plurality of proximal turns 117 and distal turns 119.

Where helical stents are used, one of the outer stent (or first stent) and inner stent (or second stent) extends generally clockwise about the longitudinal axis of the stent from one end of the stent to another, as shown in FIG. 2a and the other of the outer stent (or first stent) and inner stent (or second stent) extends in a generally counterclockwise direction about the longitudinal axis of the stent, as shown in FIG. 2b.

Other variants of the stents of FIGS. 2a and 2b may be used as well. For example, the stents may have loops which are oriented at an oblique angle relative to the longitudinal axis.

Figure 2D:
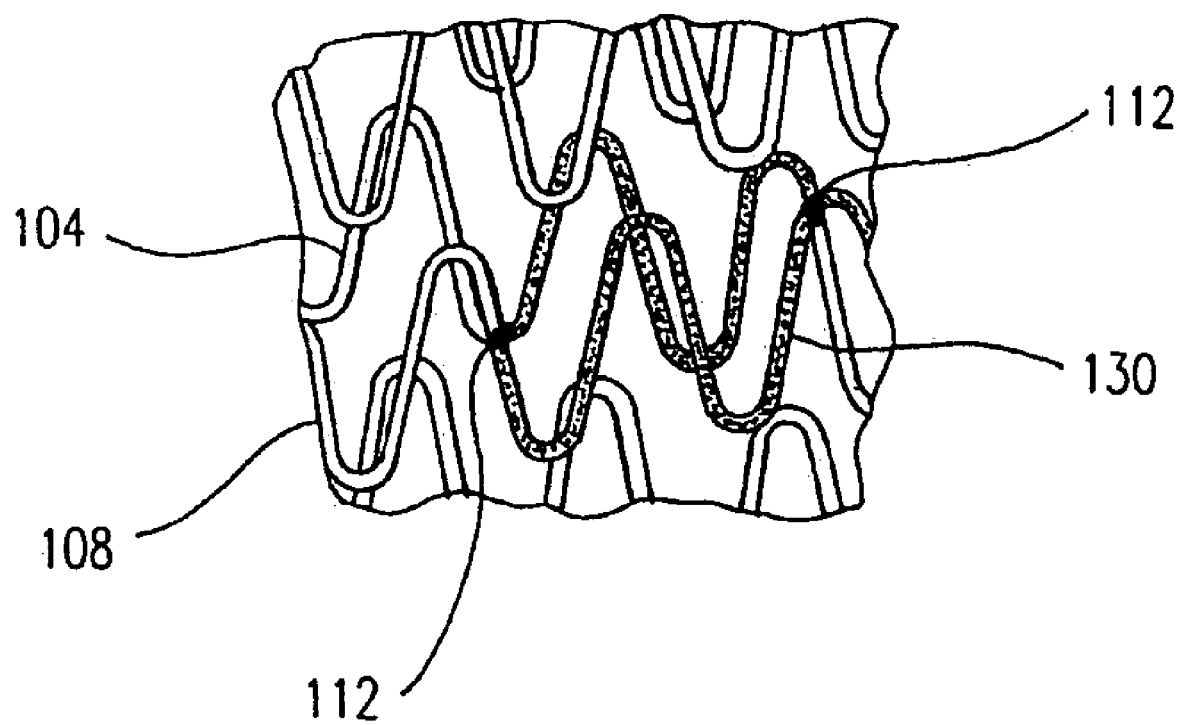
FIG. 2d is an inset of FIG. 2c showing a highlighted cell.
Figure 2E:
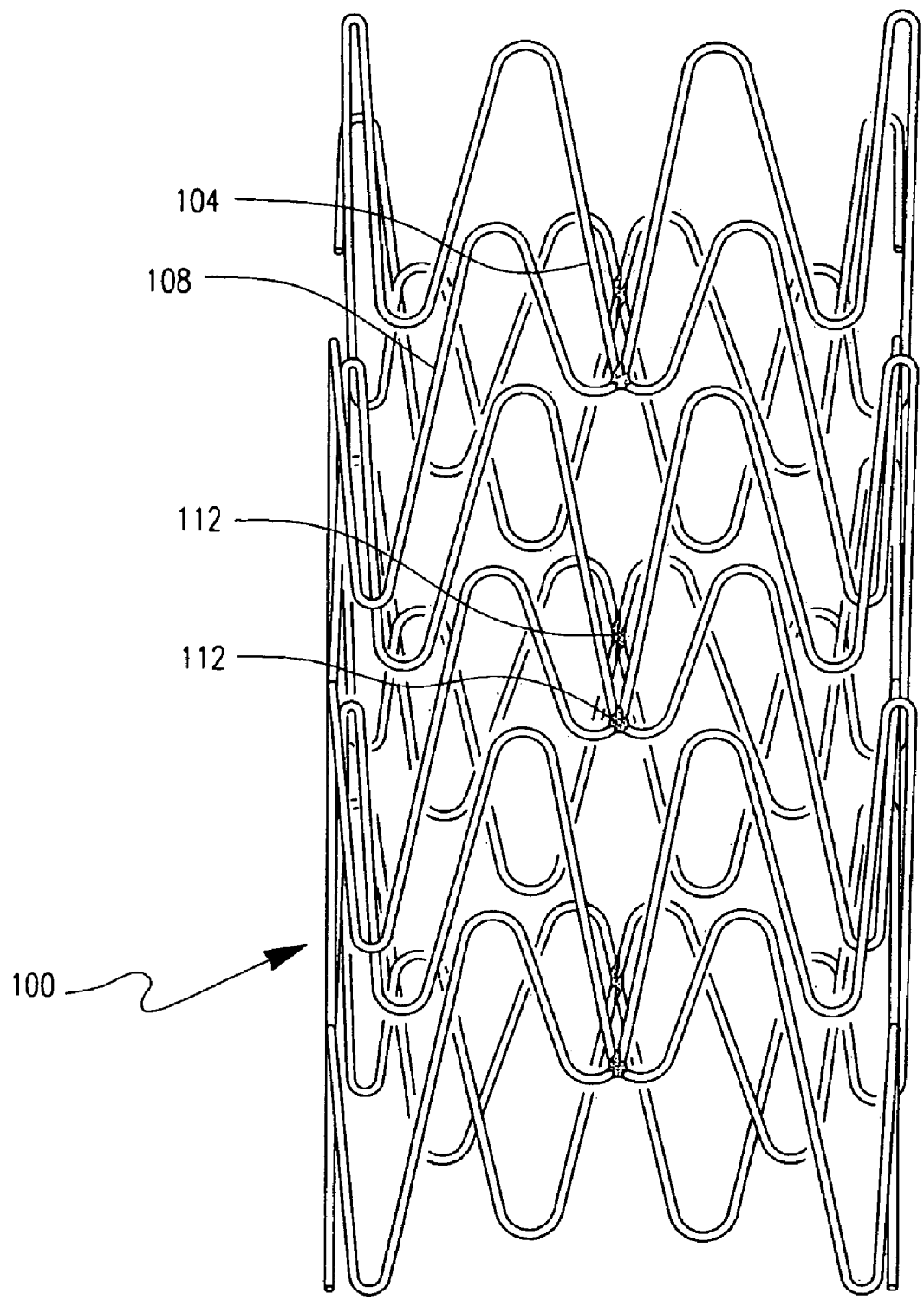
FIG. 2e shows an inventive tubular stent.

An example of an inventive device is shown in tubular form generally at 100 in FIG. 2e. The device includes an inner stent 104, an outer stent 108 and a plurality of connections 112.

It is within the scope of the invention to use other types of stents for the outer (or first) and inner (or second) stents. For example, the stent of U.S. Pat. No. 4,800,882 may be used. That stent includes a plurality of interconnected loops which extend at a perpendicular angle relative to the longitudinal axis of the stent with the loops extending only part of the way about the longitudinal axis of the stent. Two such stents may be used, each of wind in opposing directions.

Helical stents having cells may also be used for the inner stent and/or outer stent. In such a case, however, it is desirable that the helical stent with the cells not have a closed, electrically conductive pathway. Such a stent could be made by including non-conductive material, for example any of the non-conductive materials disclosed herein, in each cell of a metal stent so as to prevent the formation of an electrically conductive pathway. Desirably, the electrically non-conducting materials will be provided in portions of the stent which are subjected to compressive stress on expansion of the stent rather than in those portions of the stent which will experience tension on expansion of the stent. As such, the straight segments of a stent will be more desirable locations for the non-conductive materials than the turns of the stent.

Desirably, the tubular medical device or insert will have a plurality of cells where each cell is defined by a portion of the outer or first stent, a portion of the inner or second stent and at least two connections between the outer or first stent and the inner or second stent. An example of such a cell is highlighted in FIG. 2d, an inset of FIG. 2c. Cell 130 is formed by a portion of inner stent 104 and a portion of outer stent 108, joined together by two connections 112. The cell lies partially in the tubular envelope of the outer stent and partially in the tubular envelope of the inner stent. Cells 130 do not form a continuous, closed electrically conductive loop because the connection between the two portions of the cells is substantially electrically non-conductive.

Figure 3A:
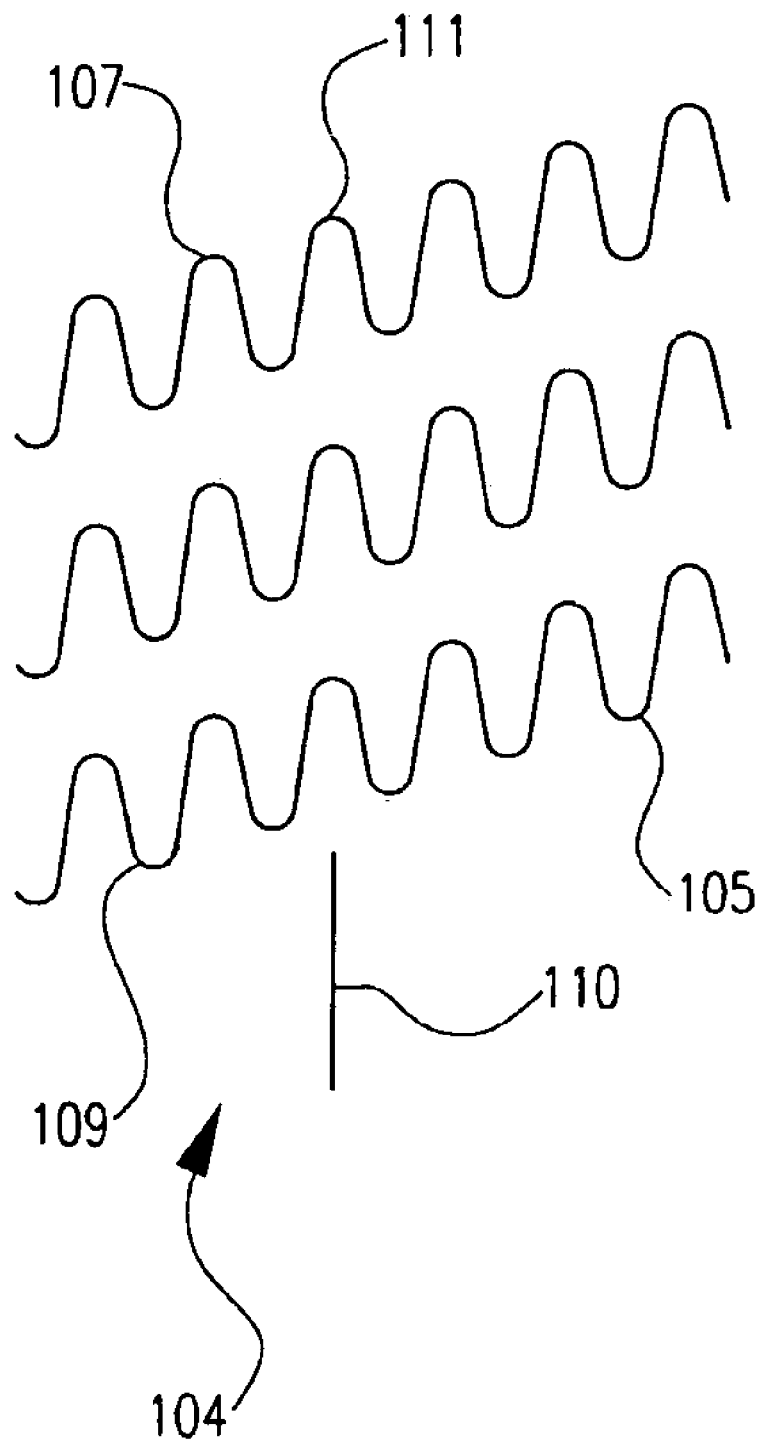
FIG. 3a shows a stent which has been cut open along a line parallel to the longitudinal axis of the stent and laid flat. The stent is for use as a component of the inventive tubular inserts.
Figure 3B:
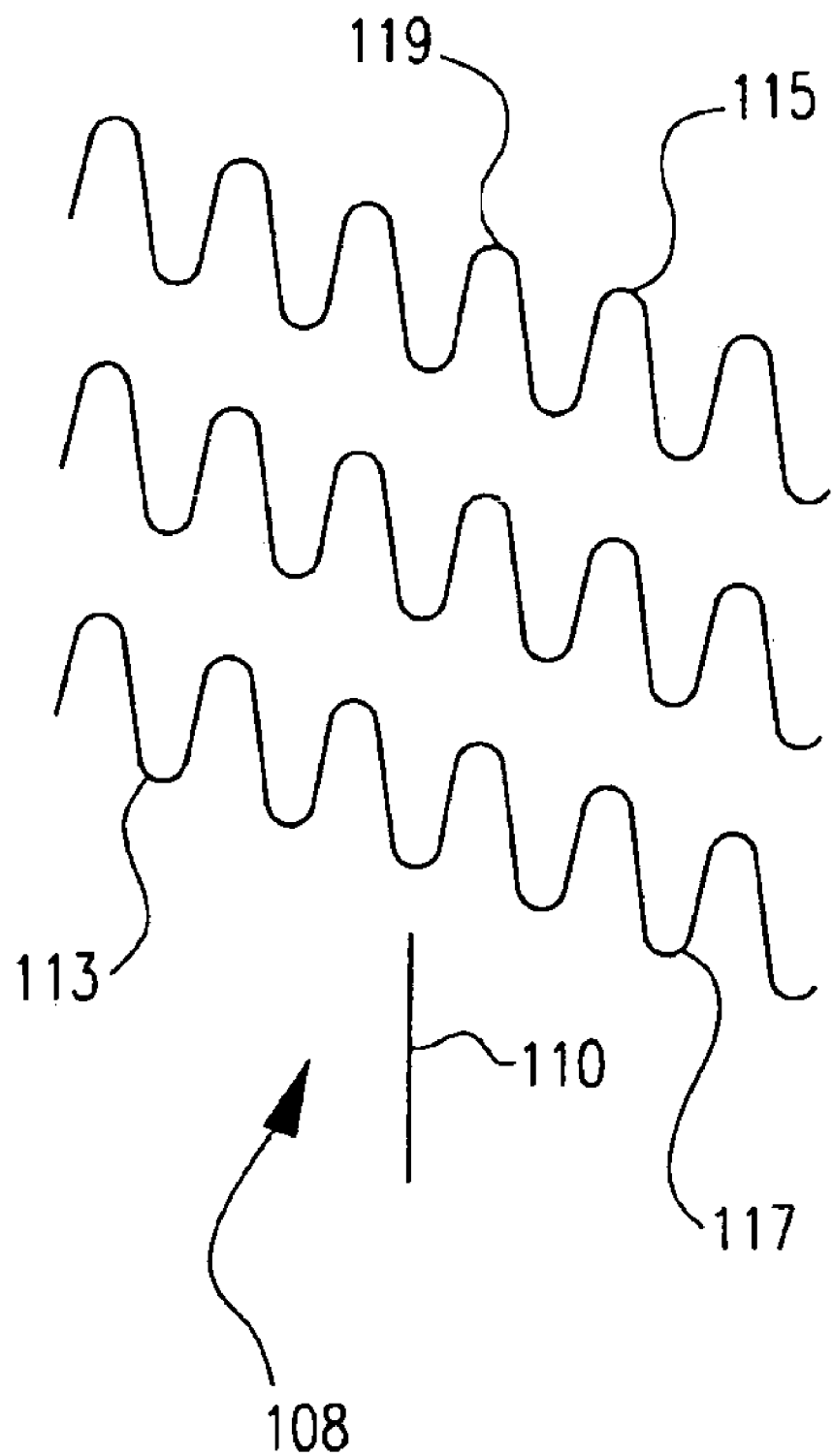
FIG. 3b shows a stent which has been cut open along a line parallel to the longitudinal axis of the stent and laid flat. The stent is for use as a component of the inventive tubular inserts.
Figure 3C:
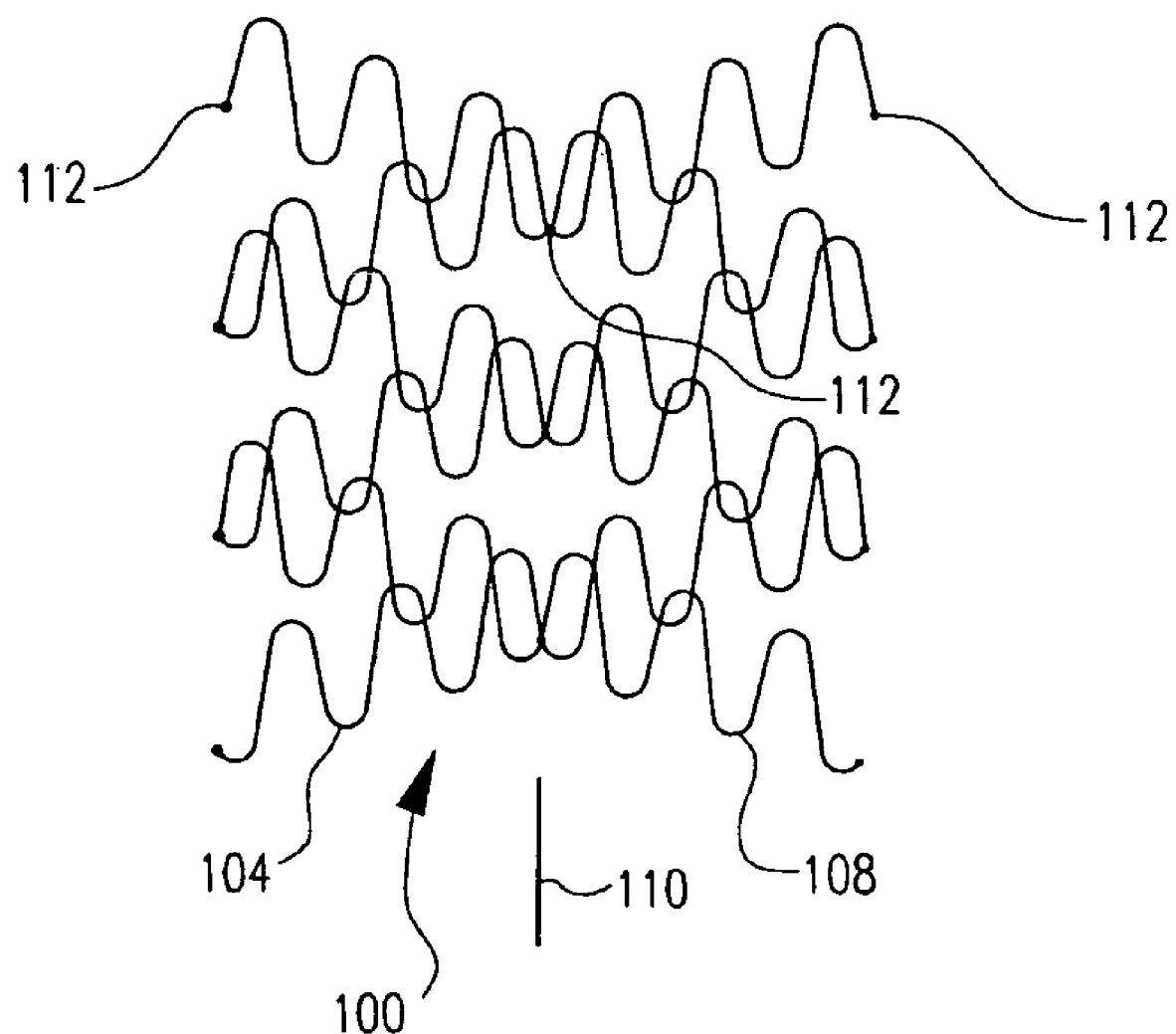
FIG. 3c shows an inventive tubular insert which has been cut open along a line parallel to the longitudinal axis of the stent and laid flat.

Another embodiment of an inventive device is shown at 100 in FIG. 3c. Tubular medical device or insert 100, shown in the flat in FIG. 3c, comprises an inner stent 104 and an outer stent 108, shown in FIGS. 3a and 3b, respectively. At least a portion of inner stent 104 is disposed within the outer stent 108. The outer stent has a longitudinal axis 110 and is constructed so as to be free of any closed loops which are electrically conductive and which are disposed about the longitudinal axis such that the longitudinal axis passes through the closed loop. The inner stent has a longitudinal axis 110 and is constructed so as to be free of any closed loops which are electrically conductive and which are disposed about the longitudinal axis such that the longitudinal axis passes through the closed loop. There is at least one and desirably, a plurality of substantially electrically non-conductive 112 connections between the inner stent and the outer stent. Desirably, where a wall surface is defined by the outer and inner stents, there are no closed, substantially electrically conductive loops in the wall surface of the tubular insert.

Inner stent 104 and outer stent 108 spiral in opposing directions and have a steeper pitch than that shown in FIGS. 2. Desirably, as shown in FIGS. 3a and 3b, the stents are mirror images of one another. The stents are arranged to overlap so as to provide one or more large openings 164 in the regions in-between where the inner and outer stents overlap with one another.

Figure 3D:
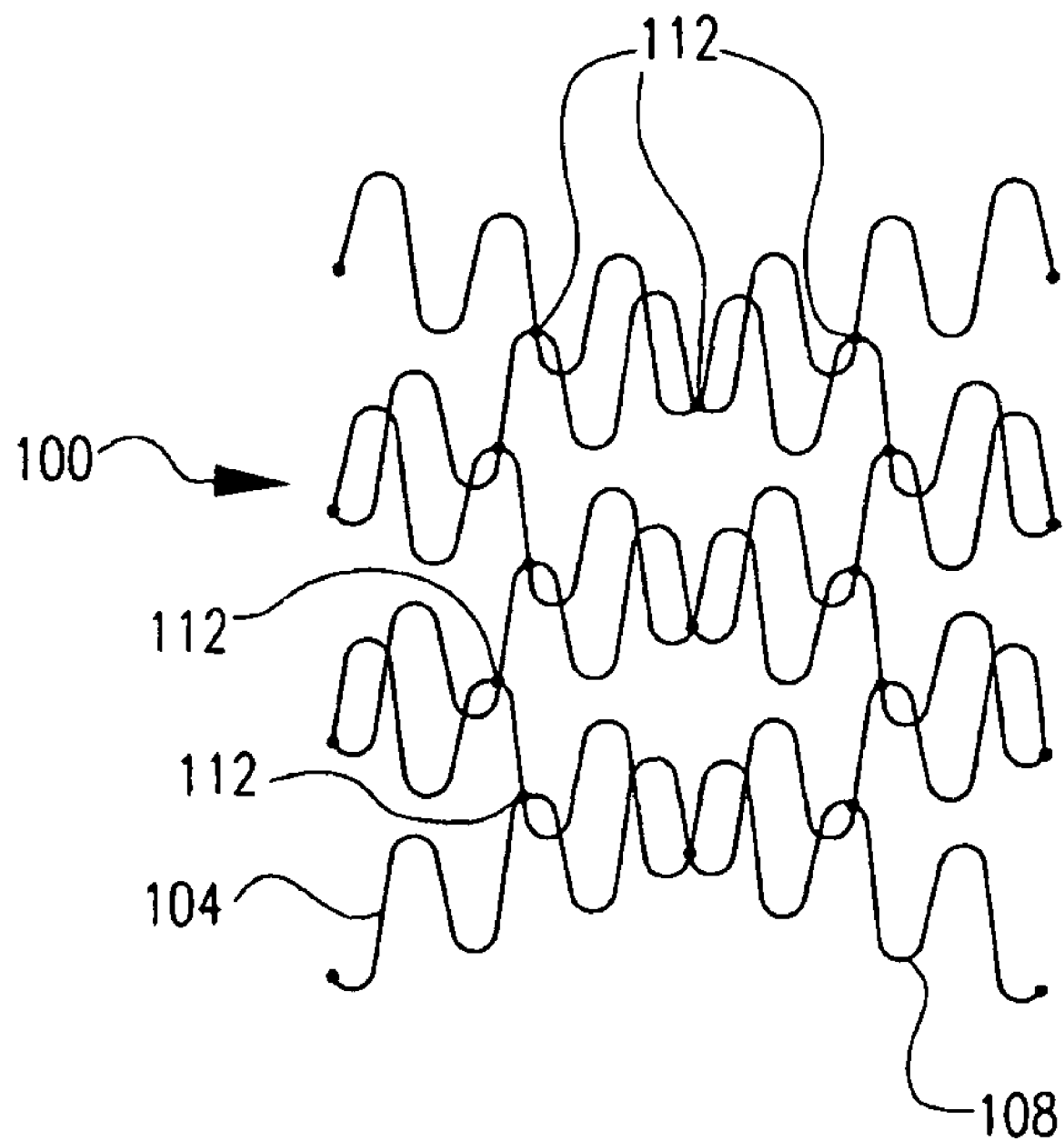
FIG. 3d shows one inventive configuration of connections between inner and an outer stents.

Desirably, the inner and outer stents will be provided with substantially electrically non-conductive connectors therebetween. An example of a suitable pattern of substantially electrically non-conductive connectors 112 is shown in FIG. 3d. In the example of FIG. 3d, connectors 112 are arranged about the periphery of large openings 164. In the example of FIG. 3c, the connectors are evenly spaced from one-another along the inner stent and are evenly spaced from one-another along the outer stent. In general, the connectors may be evenly spaced from one another or may be unevenly spaced from one another on the inner and outer stents. In both arrangements, the connectors are desirably distributed so that the resulting device lacks electrically conductive closed loops.

Figure 4A:
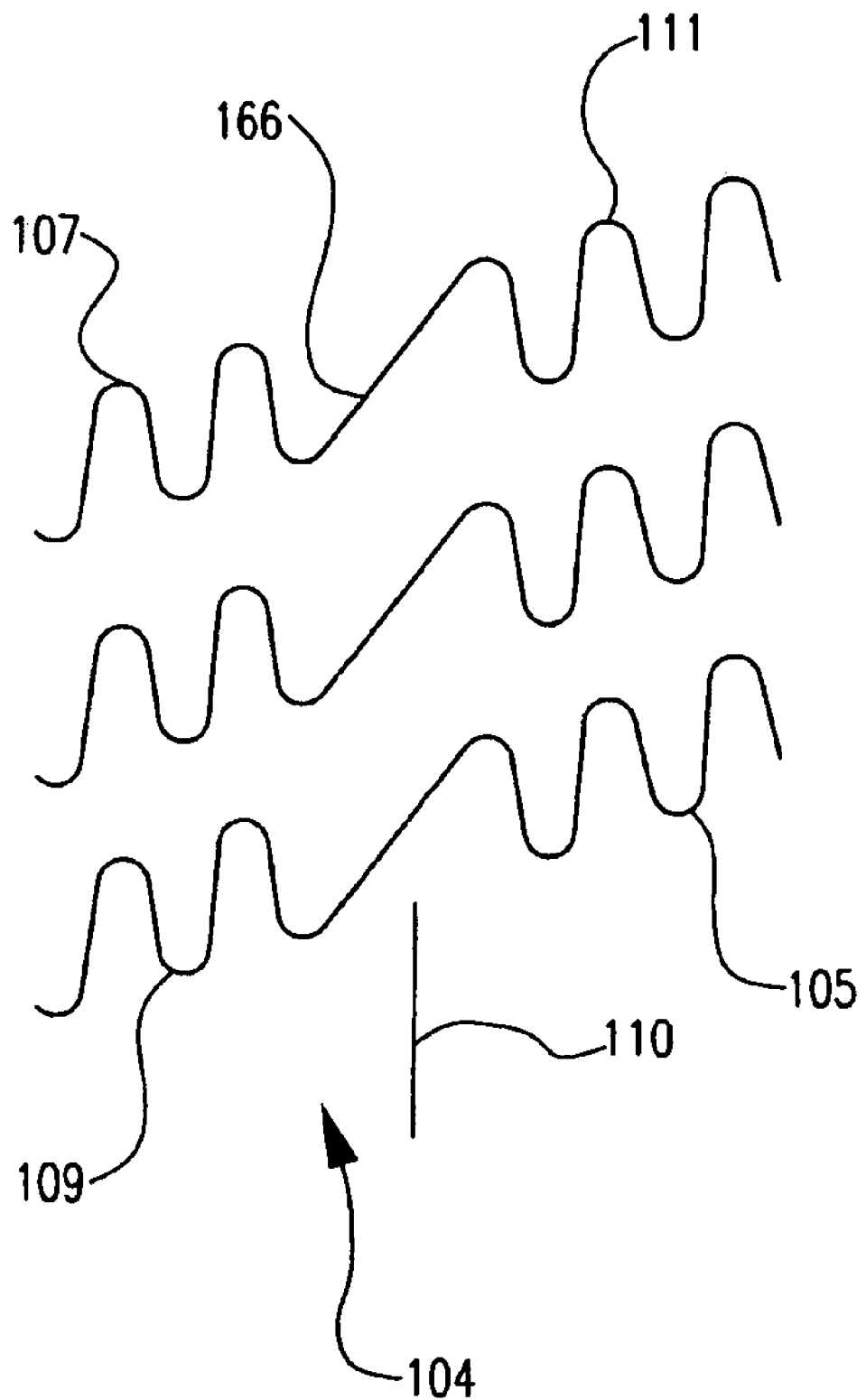
FIG. 4a shows a stent which has been cut open along a line parallel to the longitudinal axis of the stent and laid flat. The stent is for use as a component of the inventive tubular inserts.
Figure 4B:
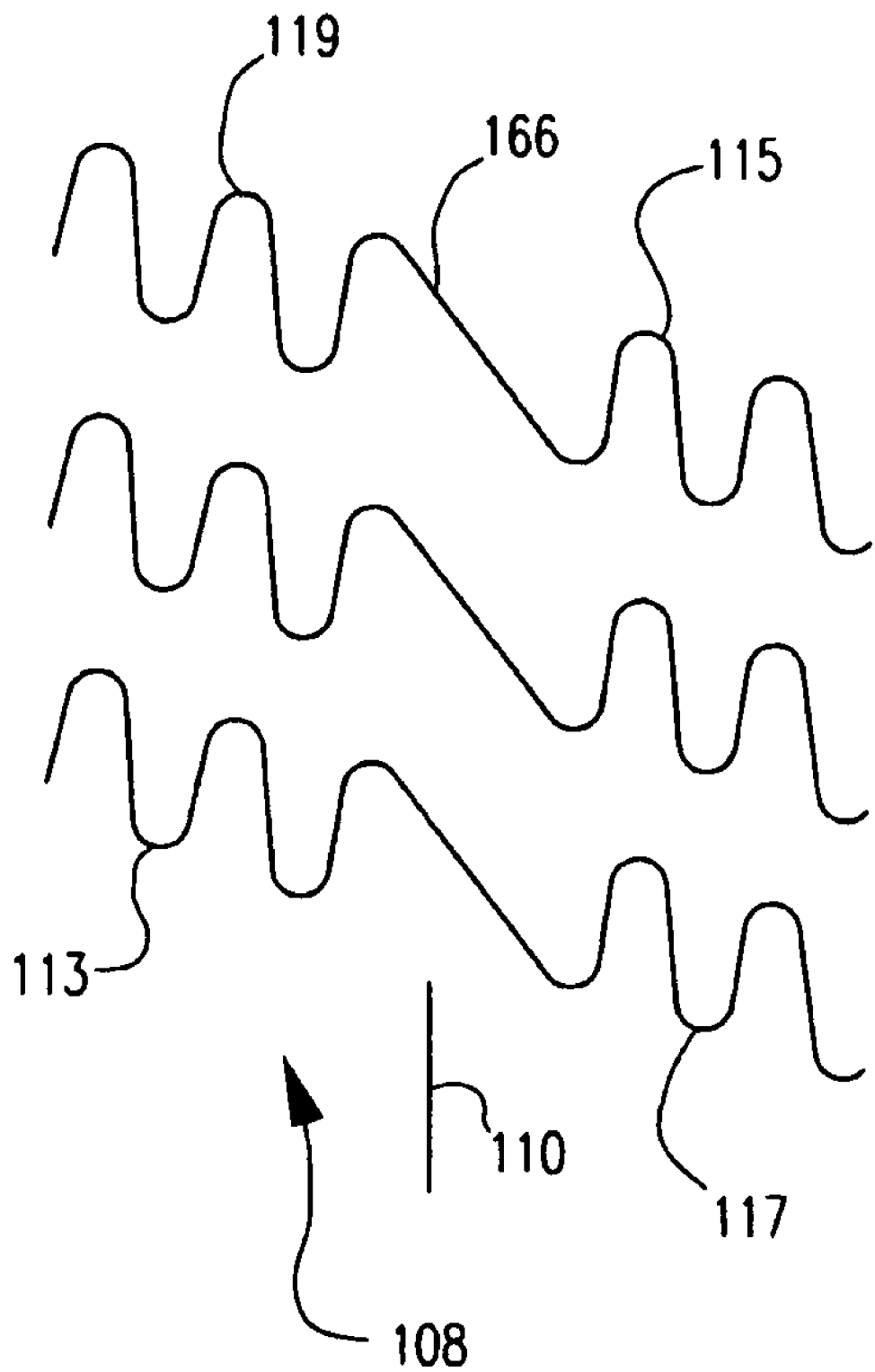
FIG. 4b shows a stent which has been cut open along a line parallel to the longitudinal axis of the stent and laid flat. The stent is for use as a component of the inventive tubular inserts.
Figure 4C:
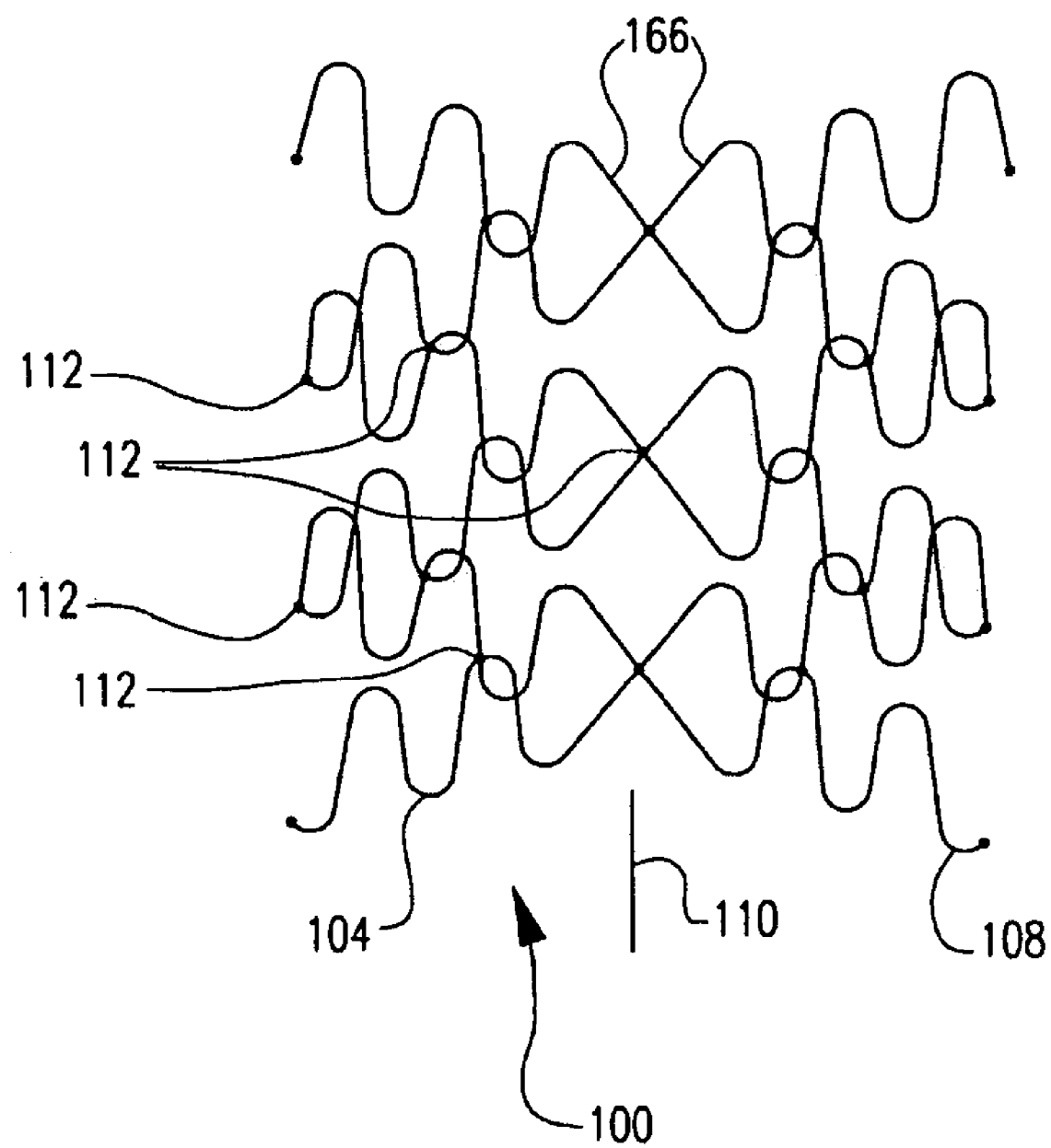
FIG. 4c shows an inventive tubular insert which has been cut open along a line parallel to the longitudinal axis of the stent and laid flat.

Yet another embodiment of the invention is shown in FIG. 4c. The insert of FIG. 4c is formed of two helical stents, inner stent 104 and outer stent 108 shown in FIGS. 4a and 4b. Desirably, the inner and outer stents will be mirror images of one another, as shown in FIGS. 4a and 4b. The stents of FIGS. 4a and 4b each have a plurality of sections where the regular pattern of bends is interrupted by a substantially straight, long segment 166. The inner and outer stents are arranged such that the substantially straight, long segments 166 of the inner and outer stents cross one another. Typically, the straight, long segments will be non-parallel to the longitudinal axis of the stent. As shown in FIG. 4c, the segments cross one another to form a structure that resembles an 'X'. The inner and outer stents are desirably connected one to the other in areas of overlap via substantially non-electrically conduction connectors. Desirably, the stents are interconnected at least in the area where the straight, long segments cross one another. The stent of FIG. 4c includes a plurality of substantially electrically non-conductive connections 112. It is also within the scope of the invention for there to be fewer connections or for there to be more connections.

Figure 5A:
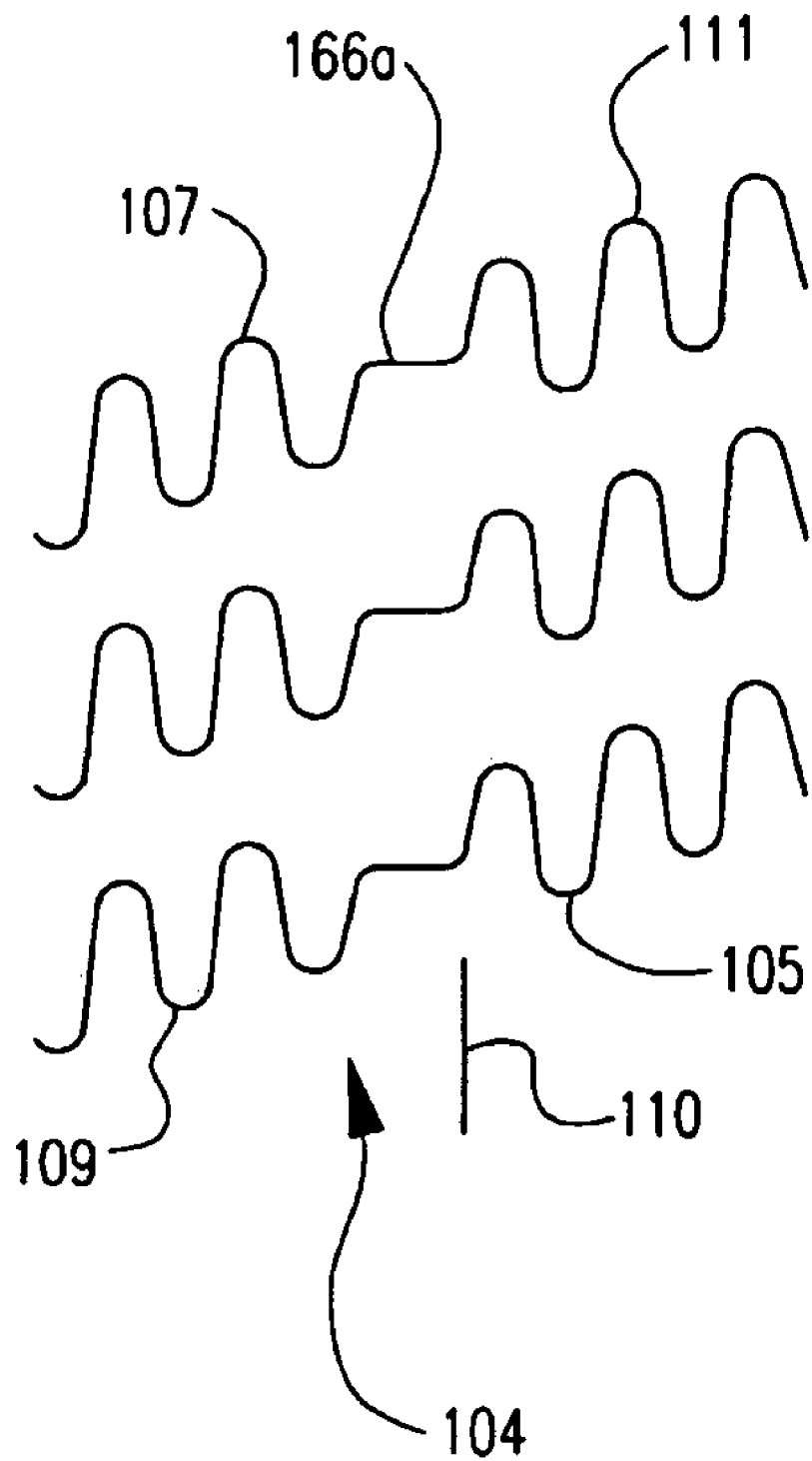
FIG. 5a shows a stent which has been cut open along a line parallel to the longitudinal axis of the stent and laid flat. The stent is for use as a component of the inventive tubular inserts.
Figure 5B:
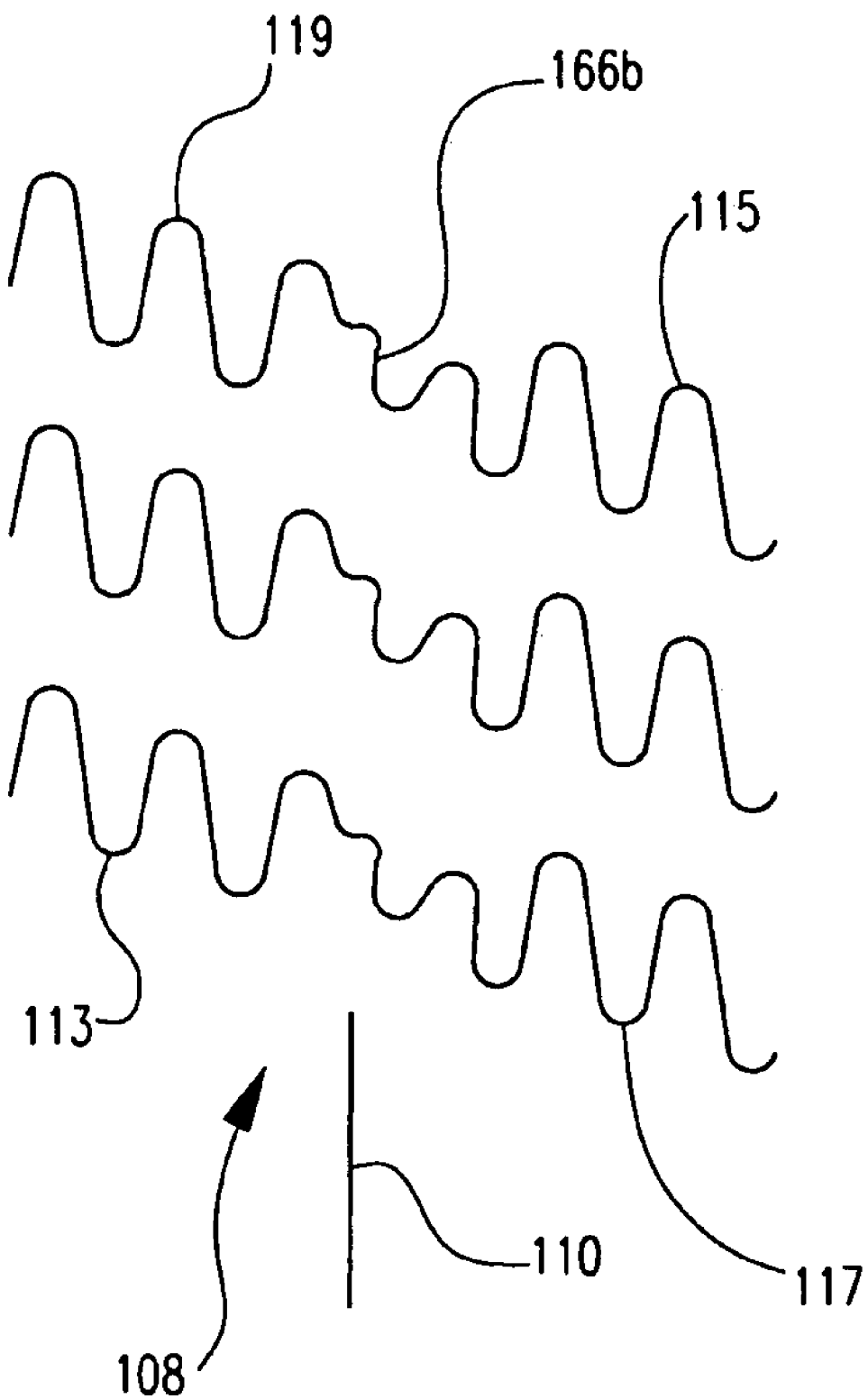
FIG. 5b shows a stent which has been cut open along a line parallel to the longitudinal axis of the stent and laid flat. The stent is for use as a component of the inventive tubular inserts.

In yet another embodiment of the invention, as shown in FIG. 5a-5c, the pattern of bends in one of the stents is interrupted by a straight section 166a which extends in a substantially circumferential direction (shown in FIG. 5a) and the pattern of bend in the other stent (FIG. 5b) is interrupted by a section which includes a portion 166b which extends substantially in the longitudinal direction. The inner and outer stents are arranged such that the substantially straight, long segments 166a of one stents crosses the portion 166b of the other stent which extends substantially in the longitudinal direction. The crossing portion defines a plurality of right angles between the circumferential and longitudinal sections of the two stents. The inner and outer stents are desirably connected one to the other in areas of overlap via substantially non-electrically conduction connectors. In the device of FIG. 5c, it is noted that the inner and outer stents are not mirror images of one another. Desirably, the stents are interconnected at least in the area where the straight, long segments cross one another, as shown in FIG. 5c. Optionally, the stents may be connected at regions of overlap so as to avoid the presence of electrically conductive loops. As shown in FIG. 5c, there are a series of connections on one side of the device and another series of connections opposite the first series of connections. Another pattern of connections is shown in FIG. 5d. The device of FIG. 5d includes additional connections in between the lines of connections which are opposite one another in the device of FIG. 5c. The devices of FIGS. 5c and 5d as well as the other devices disclosed herein may have fewer or more connections than shown in FIGS. 5c and 5d.

Figure 6A:
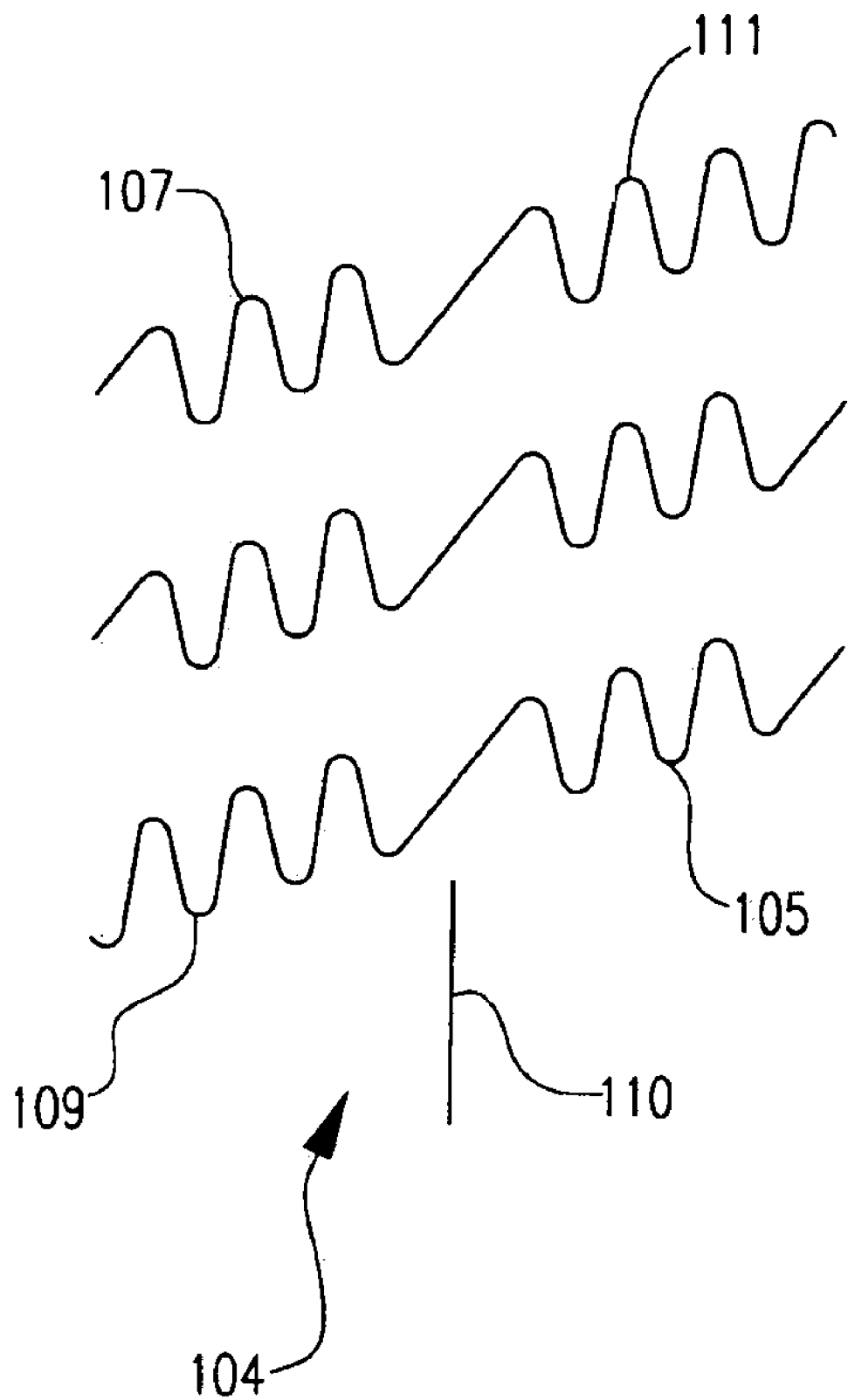
FIG. 6a shows a stent which has been cut open along a line parallel to the longitudinal axis of the stent and laid flat. The stent is for use as a component of the inventive tubular inserts.
Figure 6B:
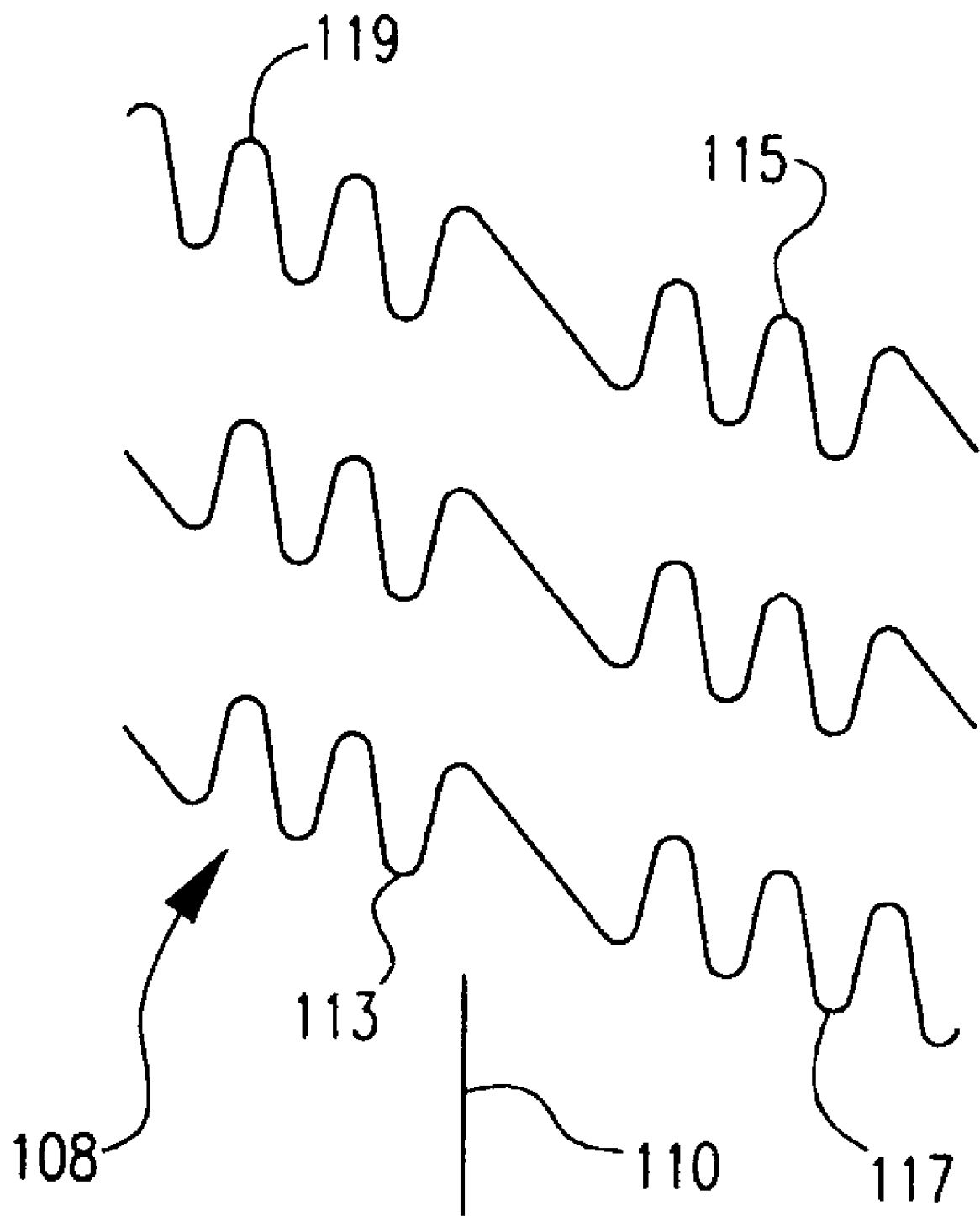
FIG. 6b shows a stent which has been cut open along a line parallel to the longitudinal axis of the stent and laid flat. The stent is for use as a component of the inventive tubular inserts.
Figure 6C:
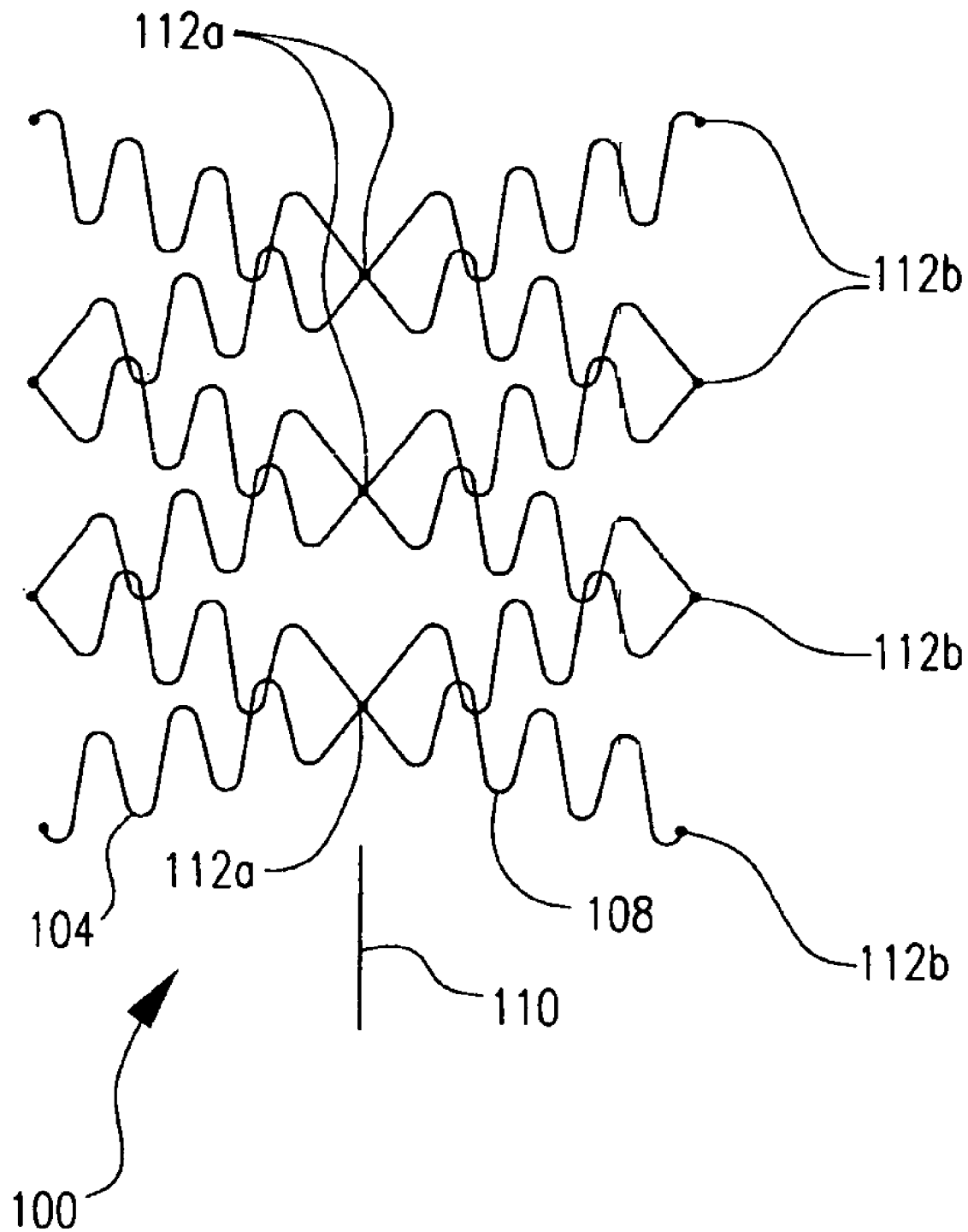
FIG. 6c shows an inventive tubular insert which has been cut open along a line parallel to the longitudinal axis of the stent and laid flat.

Yet another embodiment is shown in FIG. 6c. The device of FIG. 6c is similar to that of FIG. 4c, although the exact pattern of overlap between inner stent 104 and outer stent 108 differs with the regions of overlap more evenly spaced. In the device of FIG. 4c, there are fewer connections. A first line of connections 112a extends up one side of the stent and a second line of connections 112b extends along the device opposite the first line of connections.

Figure 7A:
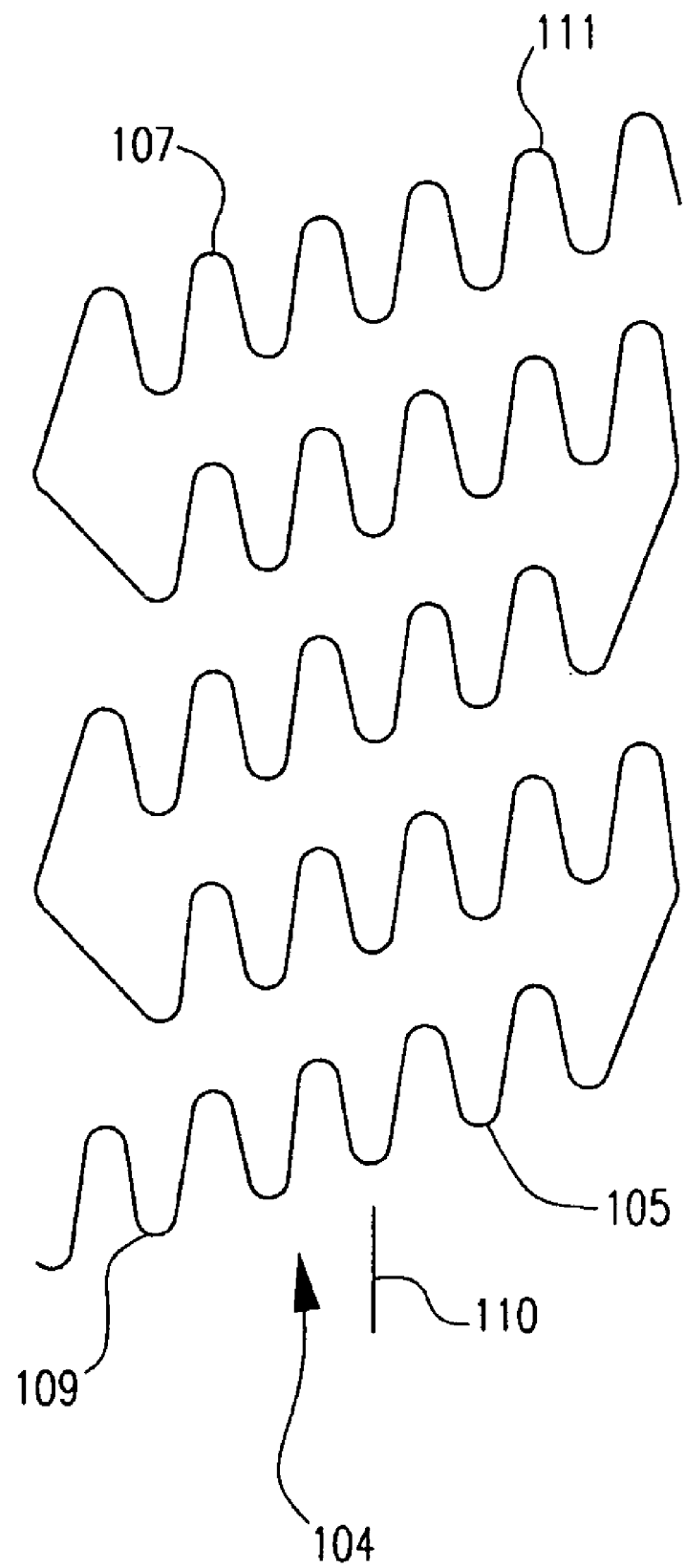
FIG. 7a shows a stent which has been cut open along a line parallel to the longitudinal axis of the stent and laid flat. The stent is for use as a component of the inventive tubular inserts.
Figure 7B:
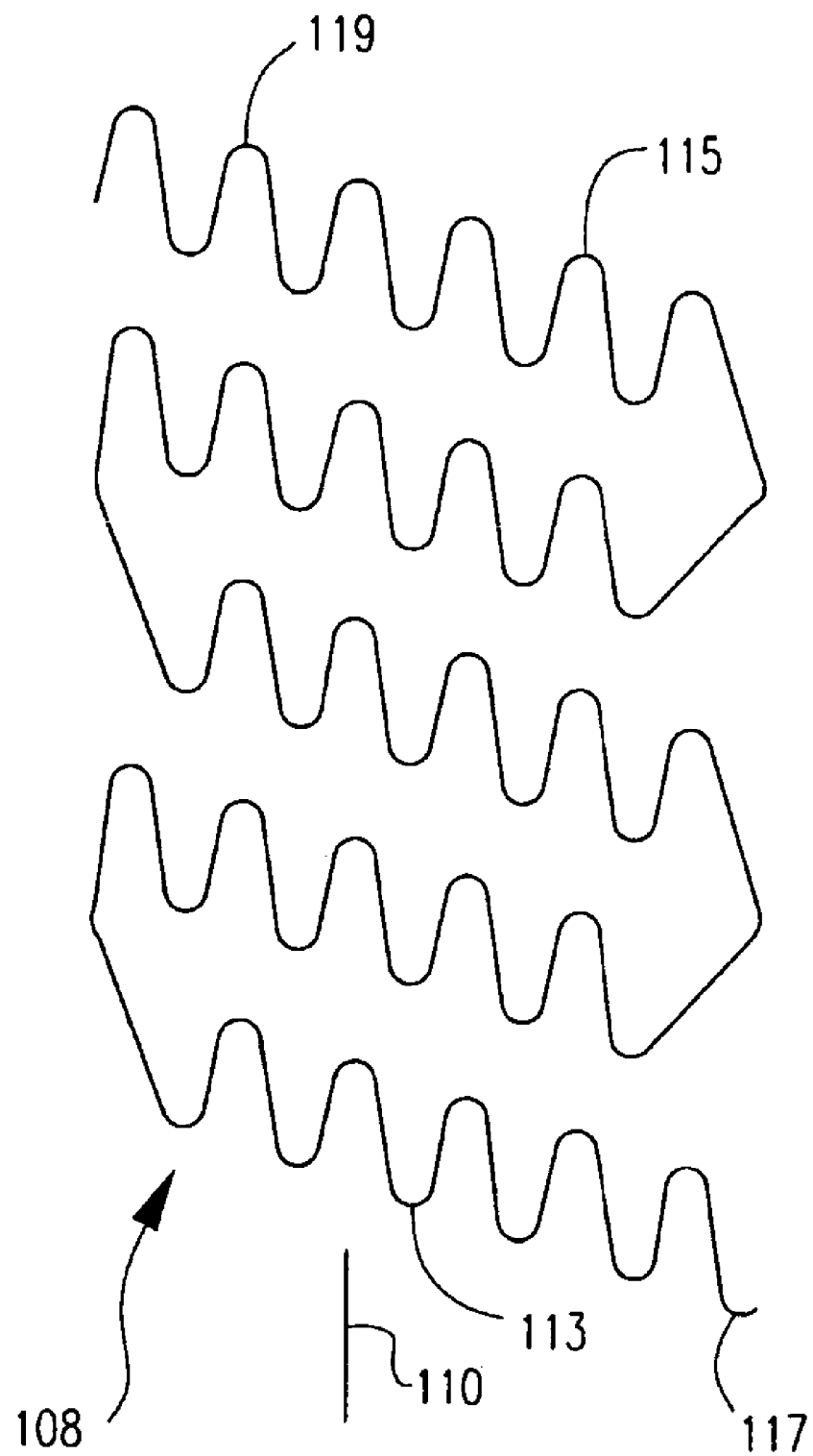
FIG. 7b shows a stent which has been cut open along a line parallel to the longitudinal axis of the stent and laid flat. The stent is for use as a component of the inventive tubular inserts.
Figure 7C:
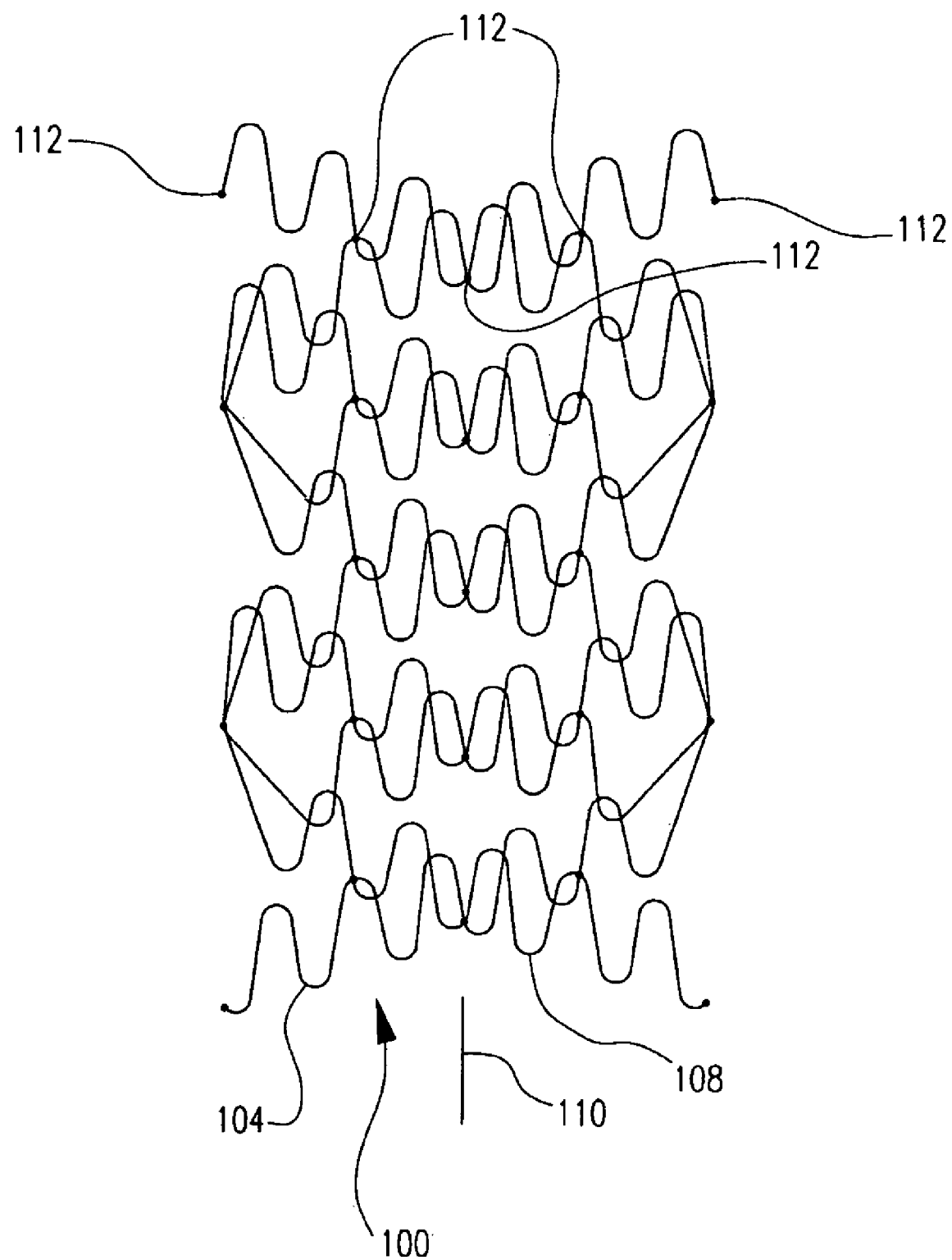
FIG. 7c shows an inventive tubular insert which has been cut open along a line parallel to the longitudinal axis of the stent and laid flat.

The inventive medical devices or inserts may also be made using overlapping stents which are not helical. An example of such a device is shown in FIG. 7c. Stents 104, shown in FIG. 7a, winds upward in a first helical direction and then winds helically downward. The upward and downward pattern is optionally repeated one or more times, as shown in FIG. 7a. The stent of FIG. 7b is a mirror of the stent of FIG. 7a. Desirably, the inner and outer stents will be connected one to the other via substantially non-electrically conducting connectors in the areas where they overlap one another, as shown in FIG. 7c, so as to avoid the presence of electrically conductive loops. In the device of FIG. 7c, the connections may be seen as forming as plurality of lines of connections which extend along the longitudinal axis.

Figure 8A:
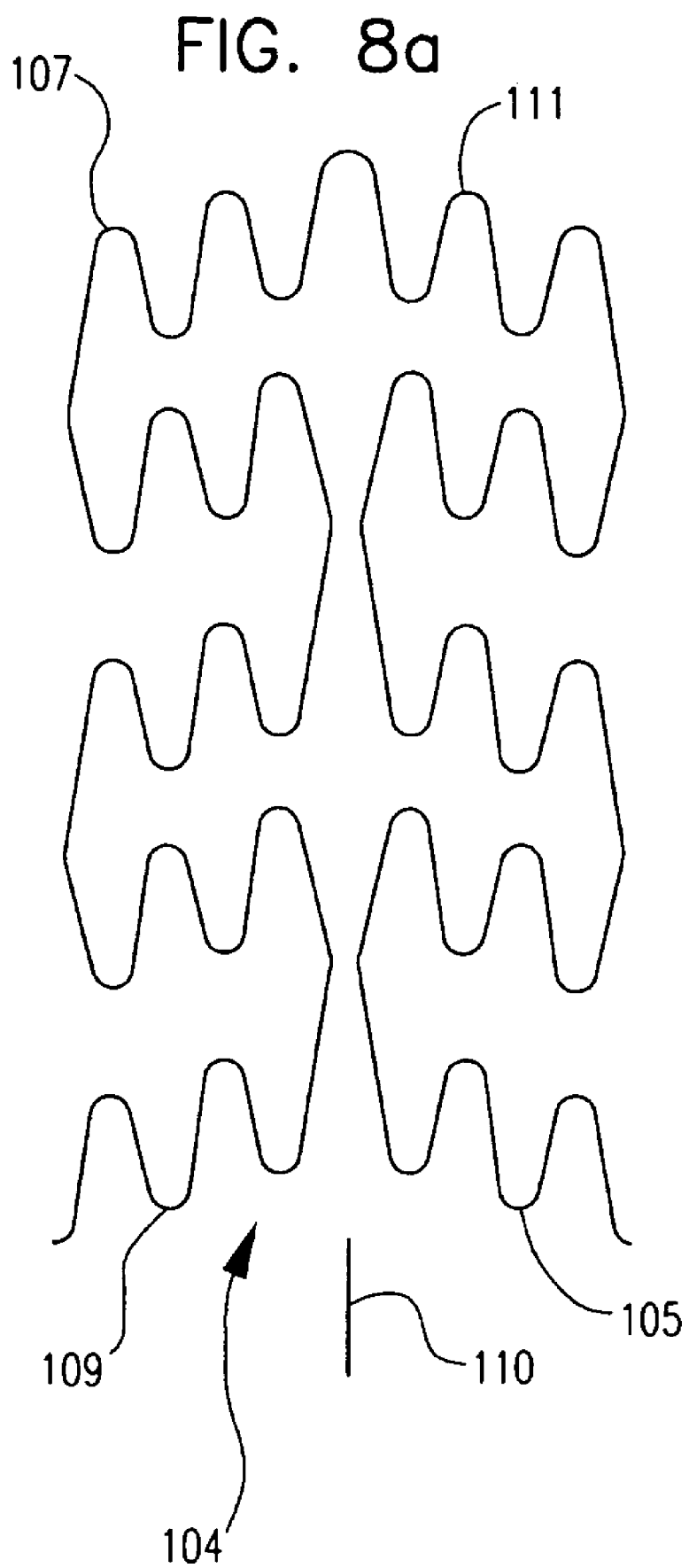
FIG. 8a shows a stent which has been cut open along a line parallel to the longitudinal axis of the stent and laid flat. The stent is for use as a component of the inventive tubular inserts.
Figure 8B:
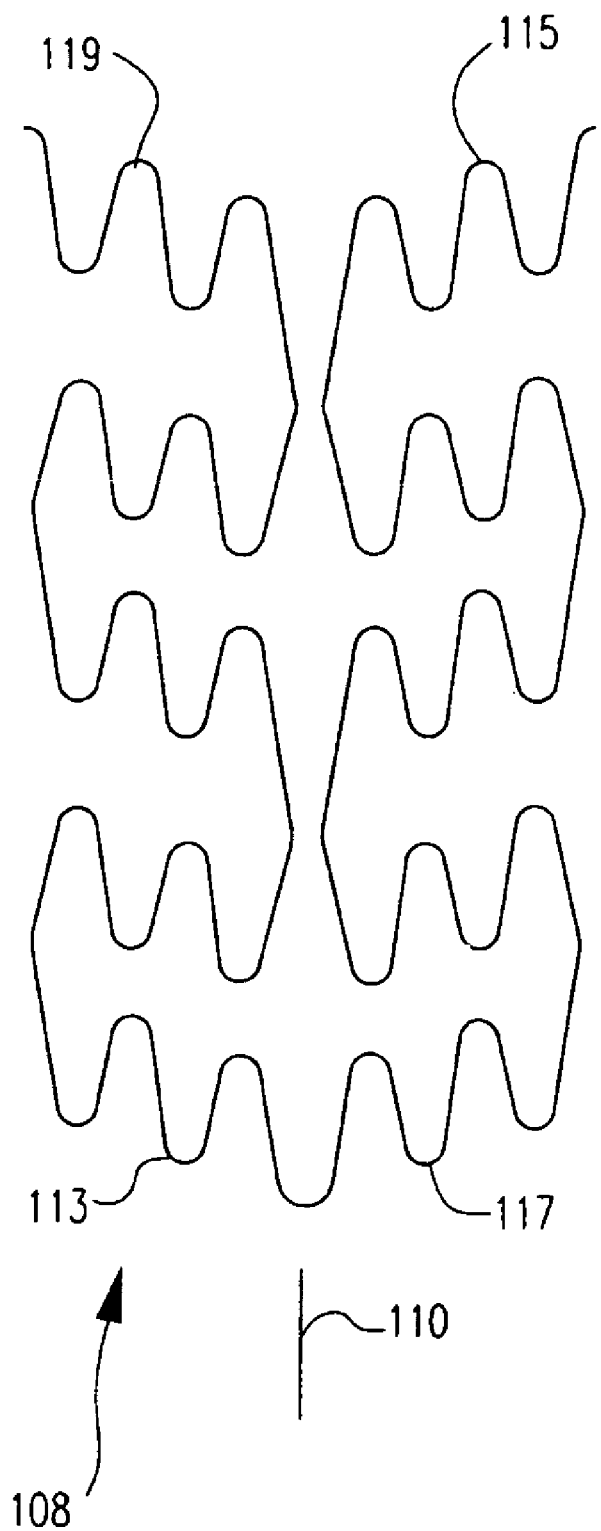
FIG. 8b shows a stent which has been cut open along a line parallel to the longitudinal axis of the stent and laid flat. The stent is for use as a component of the inventive tubular inserts.
Figure 8C:
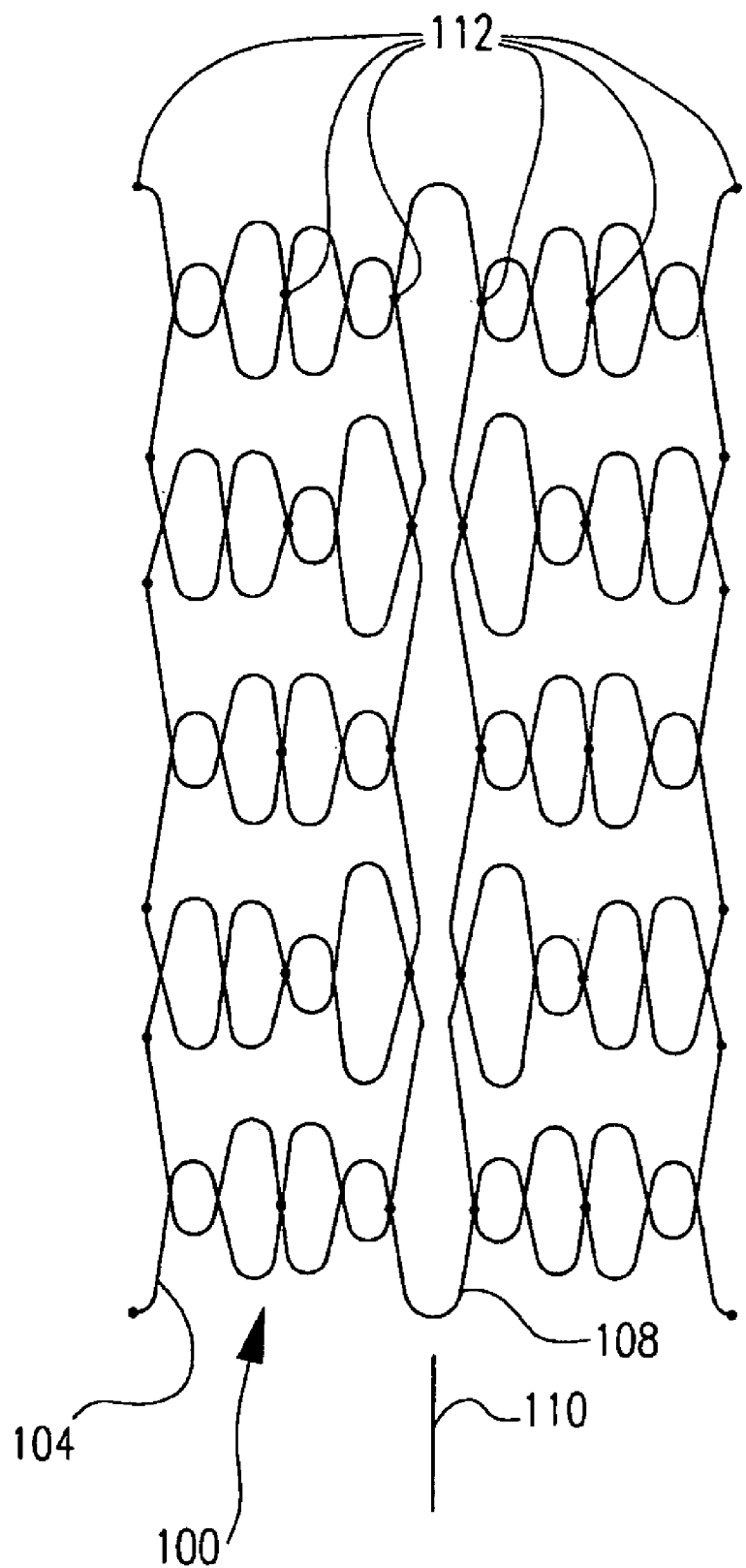
FIG. 8c shows an inventive tubular insert which has been cut open along a line parallel to the longitudinal axis of the stent and laid flat.

Yet another inventive stent is shown in FIG. 8c. The stent of FIG. 8c is made from inner stent 104, shown in FIG. 8a, and outer stent 108, shown in FIG. 8b. Each of the inner stent and the outer stent consists of a single member which winds from one end of the stent to the other end of the stent and back again. Outer stent 108 is a mirror image of inner stent 104 about an axis that is perpendicular to the longitudinal axis of the stent. Desirably, the inner stent and the outer stent will be interconnected at a plurality of locations with connectors that are substantially electrically non-conductive so as to avoid the presence of electrically conductive loops. The pattern of conections 112 as shown in FIG. 8c includes a plurality of lines of connections which extend longitudinally, The stent may also be prepared with more connections or with fewer connections.

Other arrangements of inner and outer stents are also within the scope of the invention.

Morover, the inner stent can have more undulations than the outer stent or vice versa. In those cases where the undulations may be characterized as having a frequency and an amplitude, the inner stent and outer stent may have different frequencies and/or amplitudes, or the same frequencies and/or amplitudes. The inner stent may be made of a thicker or a thinner material than the outer stent or vice versa, or they may be of the same thickness. The inner and outer stents may be made of the same material or a different material. The material of the inner stent may be wider or narrower than the material of the outer stent or of the same width.

Another example of a stent that is suitable for use as an inner stent and/or an outer stent is illustrated in FIG. 9. Connectors 205, shown as shaded, may be made of a substantially electrically non-conductive material, such as, for example, a polymeric material and at least a portion 211 (shown as hatched) of each circumferential band may include an electrically non-conductive material. More details about the use of polymeric connectors in a stent such as that shown in FIG. 1 are disclosed in U.S. Pat. No. 6,409,754. Thus, each cell 215 (shown as hatched) has at least one electrically non-conducting portion 211 and/or 205 and an electrically conductive portion 219. Similarly, each closed circumferential path about the stent includes at least one electrically non-conducting portion 211 and/or 205 and an electrically conductive portion 219. Desirably, the electrically non-conductive portions will be provided in portions of the stent which are subjected to compressive stress on expansion of the stent rather than in those portions of the stent which will experience tension on expansion of the stent. As such, the straight segments of a stent will be more desirable locations for the non-conductive materials than the turns of the stent.

Two such stents may be coupled one to another at one or more locations using an electrically non-conductive material, in an arrangement similar to that disclosed with respect to FIG. 1. The connectivity between the inner and outer stents is such as to avoid providing any electrically conductive closed loops.

The invention is also directed to an expandable member for implantation in a bodily vessel where the expandable member comprises a multilayer tubular wall surface formed of a plurality of interconnected struts disposed at different distances from a centerline which runs along a longitudinal axis of the stent. The struts define a plurality of interconnected cells, each cell including an electrically conducting portion and an electrically non-conductive portion. The tubular member includes pathways which form closed paths about the circumference of the stent, each closed path including at least one substantially electrically non-conducting portion and one electrically conducting portion. An example of such a tubular member is shown in FIG. 2e. The inventive tubular member may also be formed from a single stent which has multiple layers of struts.

In any of the inventive tubular medical devices and inserts disclosed herein as well as in any of the inventive methods disclosed herein, the substantially electrically non-conductive connection(s) between stents will typically comprise one or more plastics, adhesives, composites or ceramics or combinations thereof. In the case of a plastic, any suitable biocompatible plastic may be used. Examples of suitable plastics include but are not limited to suitable polymeric materials such as thermotropic liquid crystal polymers (LCP's). In the case of adhesives, the adhesive may be biocompatible. In the case of ceramics, the ceramics should be biocompatible. Examples of suitable ceramics include without limitation, hydroxyapatite, alumina and pyrolytic carbon. Desirably, the ceramic will be curable. Suitable materials include nitrides, oxides, silicides, and carbides. It is also with the scope of the invention for the connections to be in the form of substantially electrically non-conductive metals which are biocompatible. Additionally, any or all materials may be non-biocompatible, as long as a biocompatible coating encases the entire geometry.

Desirably, at least one and more desirably both the outer (or first) stent and the inner (or second) stent are made from a magnetic resonance compatible material. Examples of magnetic resonance compatible materials include non-ferromagnetic metals such as Elgiloy and other alloys of cobalt, chromium and nickel, Nitinol and other nickel based materials, Phynox, MP35N, titanium, titanium alloy, tantalum and tantalum alloy. The inner or second and outer or first stents may both be made of a conductive material with an electrically non-conductive material disposed thereabout.

The isolation between the first and second stents may also be achieved by providing drug and/or polymeric and/or ceramic coatings to a portion of the stents or to the entirety the stent. Where the coating(s) are provided only to portions of the stent, the coating(s) would be provided at least in the regions of contact between the two stents. Of course, the coating need be applied to only one of the two stents but it may optionally be provided to both stents. Suitable drugs and polymeric coatings include those disclosed elsewhere in this disclosure.

The invention is also directed to a method of delivering any of the inventive medical devices disclosed herein to a desired location in the body comprising disposing the medical device, for example, the tubular inserts disclosed herein, about a catheter, delivering the medical device to the desired bodily location using the catheter and deploying the medical device. Methods of deployment include allowing the medical device to self-expand in the case of self-expanding tubular inserts and using a medical balloon to expand the medical device in the case of balloon expandable tubular inserts. Balloon catheters are well known in the art. An example of a balloon catheter is disclosed in U.S. Pat. No. 6,506,201. An example of a self-expanding stent delivery catheter is disclosed in U.S. Pat. No. 6,120,522.

The inventive stents may also be used to stent bifurcated regions. A more detailed discussion of stenting bifurcated regions may be found in U.S. application Ser. No. 10/084766 as well as in U.S. Pat. No. 5,749,825 to Fischell. To that extent, the invention is also directed to a method of stenting a bifurcated region of a vessel comprising the steps of providing any of the inventive stents disclosed herein, disposing them about a catheter, delivering the stent to a bifurcated region and deploying the stent. An additional stent may be deployed through one of the cells of an inventive stent into one of the branch vessels using any suitable technique including that disclosed in U.S. Pat. No. 5,749,825.

The invention is also directed to a method of imaging a tubular medical device where the tubular medical device is in the form of an outer stent and an inner stent. At least a portion of the inner stent is disposed within the outer stent. The outer stent has a longitudinal axis and is constructed so as to be free of any closed loops which are electrically conductive and are disposed about the longitudinal axis such that the longitudinal axis passes through the closed loop. The inner stent has a longitudinal axis and is constructed so as to be free of any closed loops which are electrically conductive; and are disposed about the longitudinal axis such that the longitudinal axis passes through the closed loop. There is a substantially non-electrically conductive connection between the inner stent and the outer stent. Desirably, where a wall surface is defined by the outer and inner stents, there are no closed, substantially electrically conductive loops in the wall surface of the tubular insert. The method comprises the steps of disposing the tubular medical device within a magnetic resonance imager; using the magnetic resonance imager to obtain a magnetic resonance image of the tubular medical device and removing the tubular medical device from the magnetic resonance imager.

In one embodiment, the inventive method of imaging a tubular medical device is carried with the tubular medical device located within a living body when it is disposed within the magnetic resonance imager. In another embodiment, the tubular medical device is not located within a living body when it is disposed within the magnetic resonance imager.

The invention is also directed to a method of manufacturing a tubular medical device comprising the steps of providing a first stent and a second stent, disposing at least a portion of the second stent within the first stent and connecting the first stent and the second stent together via a connection which is substantially non-electrically conductive. The first stent has a longitudinal axis and is constructed so as to be free of any closed loops which are electrically conductive and disposed about the longitudinal axis such that the longitudinal axis passes through the closed loop. The second stent has a longitudinal axis and is constructed so as to be free of any closed loops which are electrically conductive and disposed about the longitudinal axis such that the longitudinal axis passes through the closed loop. There is a substantially non-electrically conductive connection between the first stent and the second stent. Desirably, where a wall surface is defined by the first and second stents, there are no closed, substantially electrically conductive loops in the wall surface of the tubular medical device which form a loop about the longitudinal axis. More desirably, there are no closed, substantially electrically conductive loops in the wall surface of the tubular medical device regardless of whether they extend about a longitudinal axis or a radial axis.

The stents disclosed herein may be self-expanding or balloon expandable or a hybrid of the two. In the case of a self-expanding stent, the device will be made from spring steel, a shape-memory metal such as nitinol, a shape memory polymer or any other suitable material. In the case of a balloon expandable stent, the stent may be made of metals such as stainless steel, titanium, tantalum or any other suitable material.

The invention has been discussed in particular with respect to stents. It is directed more generally to other tubular inserts as well including distal protection devices and vena cava filters. Also, the stents disclosed herein may serve as frameworks for grafts.

Any of the inventive medical devices disclosed herein may include one or more coatings and/or other delivery mechanisms which comprise one or more therapeutic agents, cellular materials, polymeric agents, drugs, etc. The coating and/or other delivery mechanism may be provided on the outer (first)

stent or portions thereof, on the inner (second) stent or portions thereof or both stents or portions thereof.

The therapeutic agent may be non-genetic or genetic. Suitable non-genetic therapeutic agents include anti-thrombogenic agents such as heparin, heparin derivatives, urokinase, and PPack (dextrophenylalanine proline arginine chloromethylketone), anti-proliferative agents such as enoxaprin, angiopeptin, or monoclonal antibodies capable of blocking smooth muscle cell proliferation, hirudin, and acetylsalicylic acid, anti-inflammatory agents such as dexamethasone, prednisolone, corticosterone, budesonide, estrogen, sulfasalazine, and mesalamine, antineoplastic/antiproliferative/anti-miotic agents such as paclitaxel, 5-fluorouracil, cisplatin, vinblastine, vincristine, epothilones, endostatin, angiostatin and thymidine kinase inhibitors, anesthetic agents such as lidocaine, bupivacaine, and ropivacaine, anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides, vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol-lowering agents; vasodilating agents; and agents which interfere with endogenous vascoactive mechanisms.

Suitable genetic materials include anti-sense DNA and RNA, DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation, the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7 are particularly desirable. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Suitable cellular materials include cells of human origin (autologous or allogeneic) or from an animal source (xenogeneic), genetically engineered if desired to deliver proteins of interest at the transplant site. The delivery media can be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (BAYHDROL®, etc.), fibrin, collagen and derivatives thereof, polysaccharides such as celluloses, starches, dextrans, alginates and derivatives, hyaluronic acid, squalene emulsions. Desirably, polyacrylic acid, available as HYDROPLUS® (Boston Scientific Corporation, Natick, Mass.), and described in U.S. Pat. No. 5,091,205, the disclosure of which is hereby incorporated herein by reference, may be used. Also desirably, the polymer may be a copolymer of polylactic acid and polycaprolactone. Other materials include selected medical-grade biodegradable materials such as PGA-TMC, Tyrosine-Derived Polycarbonates and arylates, polycaprolactone co butyl acrylate and other co polymers, Poly-L-lactic acid blends with DL-Lactic Acid, Poly(lactic acid-co-glycolic acid), polycaprolactone co PLA, polycaprolactone co butyl acrylate and other copolymers, Tyrosine-Derived Polycarbonates and arylate, poly amino acid, polyphosphazenes, polyiminocarbonates, polydimethyltrimethylcarbonates, biodegradable CA/PO4's, cyanoacrylate, 50/50 DLPLG, polydioxanone, polypropylene fumarate, or polydepsipeptides.

Other suitable coatings include macromolecules such as chitosan and Hydroxylpropylmethylcellulose. Surface erodible materials may also be used. Coatings may also comprise maleic anhydride copolymers, zinc-calcium phosphate and amorphous polyanhydrides.

The inventive medical devices may also be provided with a sugar or more generally a carbohydrate and/or a gelatin to maintain the inventive medical devices on a balloon during delivery of the medical device to a desired bodily location. Other suitable compounds for treating the inventive medical devices include biodegradable polymers and polymers which are dissolvable in bodily fluids. Portions of the interior and/or exterior of the inventive medical devices may be coated or impregnated with the compound. Mechanical retention devices may also be used to maintain the inventive medical devices on the balloon during delivery.

The inventive medical devices may also be provided in whole or in part with one or more of the above therapeutic agents, polymeric coatings or the like. Where multiple therapeutic agents are provided, different coatings and/or mechanisms may release the drugs at different rates. For example, one therapeutic agent may be released at a fast rate and another therapeutic agent may be released at a slow rate. Where multiple polymeric coatings are provided, the coatings may degrade or erode at different rates.

The inventive medical devices disclosed herein may also be provided with radiopaque markers. The radiopacity may be provided through any suitable process known in the art including but not limited to using a radiopaque coating, for example a noble metal coating such as gold, affixing a radiopaque marker to the stent or providing an area of the stent with an enlarged mass of metal as compared with the remainder of the stent.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A medical device comprising a first stent and a second stent, each of the first and second stents comprising a plurality of serpentine bands, each of the serpentine bands of the first stent comprising distal turns and proximal turns and each of the serpentine bands of the second stent comprising distal turns and proximal turns, the second stent being a mirror image of the first stent, the first stent disposed about the second stent, wherein the first stent is helical and the second stent is helical;

the serpentine bands of the first stent comprising a plurality of turns interconnected by substantially straight portions and the serpentine bands of the second stent comprising a plurality of turns interconnected by substantially straight portions;

at least one of the substantially straight portions of the first stent comprising a substantially straight, long segment and at least one of the substantially straight portions of the second stent comprising a substantially straight, long segment;

the substantially straight, long segment of the first stent overlapping the substantially straight, long segment of the second stent, the second stent being connected to the first stent at the overlap;

wherein the at least one substantially straight, long segment of the first stent is perpendicular to the at least one substantially straight, long segment of the second stent at the overlap.

2. A medical device comprising a first stent and a second stent, each of the first and second stents comprising a plurality of serpentine bands, each of the serpentine bands of the first stent comprising distal turns and proximal turns and each of the serpentine bands of the second stent comprising distal turns and proximal turns, the second stent being a mirror image of the first stent, the first stent disposed about the second stent, wherein the first stent is helical and the second stent is helical, the serpentine bands of the first stent comprising a plurality of turns interconnected by substantially straight portions and the serpentine bands of the second stent comprising a plurality of turns interconnected, wherein at least one of the substantially straight portions of the first stent overlaps at least one of the substantially straight portions of the second stent forming an acute angle therebetween.

\* \* \* \* \*

UNITED STATES PATENT AND TRADEMARK OFFICE
CERTIFICATE OF CORRECTION

| | | |
|---|---|---|
| PATENT NO. | : 7,942,923 B2 | Page 1 of 1 |
| APPLICATION NO. | : 11/120916 | |
| DATED | : May 17, 2011 | |
| INVENTOR(S) | : Daniel Gregorich | |

It is certified that error appears in the above-identified patent and that said Letters Patent is hereby corrected as shown below:

Claim 2, at column 14, line 31, the text "interconnected," should be replaced by the text --interconnected by substantially straight portions,--.

Signed and Sealed this
Thirteenth Day of March, 2012

David J. Kappos
*Director of the United States Patent and Trademark Office*